United States Patent
Libbus et al.

(10) Patent No.: US 9,526,898 B2
(45) Date of Patent: Dec. 27, 2016

(54) IMPLANTABLE NEUROSTIMULATOR FOR PROVIDING ELECTRICAL STIMULATION OF CERVICAL VAGUS NERVES FOR TREATMENT OF CHRONIC CARDIAC DYSFUNCTION WITH BOUNDED TITRATION

(71) Applicant: CYBERONICS, INC., Houston, TX (US)

(72) Inventors: Imad Libbus, St. Paul, MN (US); Badri Amurthur, Los Gatos, CA (US); Bruce H. KenKnight, Maple Grove, MN (US)

(73) Assignee: CYBERONICS, INC., Houston, TX (US)

( * ) Notice: Subject to any disclaimer, the term of this patent is extended or adjusted under 35 U.S.C. 154(b) by 0 days.

(21) Appl. No.: 14/591,349

(22) Filed: Jan. 7, 2015

(65) Prior Publication Data

US 2015/0119959 A1 Apr. 30, 2015

Related U.S. Application Data

(60) Continuation of application No. 14/179,813, filed on Feb. 13, 2014, now Pat. No. 8,965,522, which is a
(Continued)

(51) Int. Cl.
*A61N 1/36* (2006.01)
*A61N 1/362* (2006.01)
(Continued)

(52) U.S. Cl.
CPC ......... *A61N 1/36157* (2013.01); *A61N 1/0551* (2013.01); *A61N 1/362* (2013.01);
(Continued)

(58) Field of Classification Search
CPC .............. A61N 1/36157; A61N 1/0551; A61N 1/36114; A61N 1/36135; A61N 1/362; A61N 1/37235; A61N 1/36175
(Continued)

(56) References Cited

U.S. PATENT DOCUMENTS 5,330,507 A 7/1994 Schwartz
5,522,854 A 6/1996 Ideker et al.
(Continued)

FOREIGN PATENT DOCUMENTS

WO WO2010005482 A1 1/2010

OTHER PUBLICATIONS

PCT Application No. PCT/US2012/068205, Search Report and Written Opinion dated Feb. 8, 2013, 15 pages.
(Continued)

*Primary Examiner* — Paula J Stice
(74) *Attorney, Agent, or Firm* — Foley & Lardner LLP

(57) ABSTRACT

A system for providing electrical stimulation of cervical vagus nerves for treatment of chronic cardiac dysfunction with bounded titration is provided. The system includes a patient-operable external controller to transmit a plurality of unique signals. The system further includes an implantable neurostimulator, which includes a recordable memory storing an autotitration operating mode that includes a maximum stimulation intensity and is configured to increase an intensity of the delivered electrical therapeutic stimulation up to a level not exceeding the maximum stimulation intensity upon receipt of one of the unique signals.

20 Claims, 6 Drawing Sheets

Related U.S. Application Data division of application No. 13/931,961, filed on Jun. 30, 2013, now Pat. No. 8,700,150, which is a continuation-in-part of application No. 13/352,244, filed on Jan. 17, 2012, now Pat. No. 8,571,654.

(51) Int. Cl.
*A61N 1/05* (2006.01)
*A61N 1/372* (2006.01)

(52) U.S. Cl.
CPC ...... *A61N 1/36053* (2013.01); *A61N 1/36114* (2013.01); *A61N 1/36132* (2013.01); *A61N 1/36135* (2013.01); *A61N 1/37235* (2013.01)

(58) Field of Classification Search
USPC .......................................................... 607/9
See application file for complete search history.

(56) References Cited

U.S. PATENT DOCUMENTS

| | | | |
|---|---|---|---|
| 5,707,400 | A | 1/1998 | Terry, Jr. et al. |
| 5,928,272 | A | 7/1999 | Adkins et al. |
| 5,978,709 | A | 11/1999 | Begemann et al. |
| 6,006,134 | A | 12/1999 | Hill et al. |
| 6,266,564 | B1 | 7/2001 | Hill et al. |
| 6,354,991 | B1 | 3/2002 | Gross et al. |
| 6,449,507 | B1 | 9/2002 | Hill et al. |
| 6,473,644 | B1 | 10/2002 | Terry, Jr. et al. |
| 6,508,771 | B1 | 1/2003 | Padmanabhan et al. |
| 6,522,926 | B1 | 2/2003 | Kieval et al. |
| 6,600,954 | B2 | 7/2003 | Cohen et al. |
| 6,610,713 | B2 | 8/2003 | Tracey |
| 6,616,624 | B1 | 9/2003 | Kieval |
| 6,622,041 | B2 | 9/2003 | Terry, Jr. et al. |
| 6,652,449 | B1 | 11/2003 | Gross et al. |
| 6,684,105 | B2 | 1/2004 | Cohen et al. |
| 6,690,971 | B2 | 2/2004 | Schauerte et al. |
| 6,712,772 | B2 | 3/2004 | Cohen et al. |
| 6,718,208 | B2 | 4/2004 | Hill et al. |
| 6,838,471 | B2 | 1/2005 | Tracey |
| 6,839,594 | B2 | 1/2005 | Cohen et al. |
| 6,850,801 | B2 | 2/2005 | Kieval et al. |
| 6,862,480 | B2 | 3/2005 | Cohen et al. |
| 6,892,098 | B2 | 5/2005 | Ayal et al. |
| 6,896,651 | B2 | 5/2005 | Gross et al. |
| 6,904,318 | B2 | 6/2005 | Hill et al. |
| 6,907,295 | B2 | 6/2005 | Gross et al. |
| 6,963,773 | B2 | 11/2005 | Borschowa et al. |
| 6,963,779 | B1 | 11/2005 | Shankar |
| 6,985,774 | B2 | 1/2006 | Kieval et al. |
| 7,010,345 | B2 | 3/2006 | Hill et al. |
| 7,072,720 | B2 | 7/2006 | Puskas |
| 7,123,961 | B1 | 10/2006 | Kroll et al. |
| 7,136,705 | B1 | 11/2006 | Park |
| 7,139,607 | B1 | 11/2006 | Shelchuk |
| 7,158,832 | B2 | 1/2007 | Kieval et al. |
| 7,184,828 | B2 | 2/2007 | Hill et al. |
| 7,184,829 | B2 | 2/2007 | Hill et al. |
| 7,189,204 | B2 | 3/2007 | Ni et al. |
| 7,218,964 | B2 | 5/2007 | Hill et al. |
| 7,221,979 | B2 | 5/2007 | Zhou et al. |
| 7,225,017 | B1 | 5/2007 | Shelchuk |
| 7,225,019 | B2 | 5/2007 | Jahns et al. |
| 7,237,320 | B2 | 7/2007 | Lam |
| 7,245,967 | B1 | 7/2007 | Shelchuk |
| 7,260,431 | B2 | 8/2007 | Libbus et al. |
| 7,269,457 | B2 | 9/2007 | Shafer et al. |
| 7,277,761 | B2 | 10/2007 | Shelchuk |
| 7,295,881 | B2 | 11/2007 | Cohen et al. |
| 7,305,265 | B2 | 12/2007 | Fukui |
| 7,321,793 | B2 | 1/2008 | Ben Ezra et al. |
| 7,324,853 | B2 | 1/2008 | Ayal et al. |
| 7,336,997 | B2 | 2/2008 | Fukui |
| 7,346,398 | B2 | 3/2008 | Gross et al. |
| 7,387,603 | B2 | 6/2008 | Gross et al. |
| 7,389,149 | B2 | 6/2008 | Rossing et al. |
| 7,395,119 | B2 | 7/2008 | Hagen et al. |
| 7,403,819 | B1 | 7/2008 | Shelchuk et al. |
| 7,418,292 | B2 | 8/2008 | Shafer |
| 7,452,800 | B2 | 11/2008 | Sosnowchik et al. |
| 7,480,532 | B2 | 1/2009 | Kieval et al. |
| 7,481,759 | B2 | 1/2009 | Whitehurst et al. |
| 7,485,104 | B2 | 2/2009 | Kieval |
| 7,493,167 | B2 | 2/2009 | Hussein et al. |
| 7,499,742 | B2 | 3/2009 | Bolea et al. |
| 7,499,747 | B2 | 3/2009 | Kieval et al. |
| 7,499,748 | B2 | 3/2009 | Moffitt et al. |
| 7,502,650 | B2 | 3/2009 | Kieval |
| 7,542,800 | B2 | 6/2009 | Libbus et al. |
| 7,548,780 | B2 | 6/2009 | Libbus et al. |
| 7,551,958 | B2 | 6/2009 | Libbus et al. |
| 7,561,922 | B2 | 7/2009 | Cohen et al. |
| 7,561,923 | B2 | 7/2009 | Libbus et al. |
| 7,570,999 | B2 | 8/2009 | Libbus et al. |
| 7,582,053 | B2 | 9/2009 | Gross et al. |
| 7,584,004 | B2 | 9/2009 | Caparso et al. |
| 7,587,238 | B2 | 9/2009 | Moffitt et al. |
| 7,606,622 | B2 | 10/2009 | Reeve |
| 7,613,511 | B2 | 11/2009 | Wu et al. |
| 7,613,516 | B2 | 11/2009 | Cohen et al. |
| 7,616,990 | B2 | 11/2009 | Chavan et al. |
| 7,617,003 | B2 | 11/2009 | Caparso et al. |
| 7,623,926 | B2 | 11/2009 | Rossing et al. |
| 7,627,384 | B2 | 12/2009 | Ayal et al. |
| 7,628,750 | B2 | 12/2009 | Cohen et al. |
| 7,630,760 | B2 | 12/2009 | Libbus et al. |
| 7,634,315 | B2 | 12/2009 | Cholette |
| 7,634,317 | B2 | 12/2009 | Ben-David et al. |
| 7,640,057 | B2 | 12/2009 | Libbus et al. |
| 7,647,101 | B2 | 1/2010 | Libbus et al. |
| 7,647,114 | B2 | 1/2010 | Libbus |
| 7,650,190 | B2 | 1/2010 | Zhou et al. |
| 7,657,312 | B2 | 2/2010 | Pastore |
| 7,660,628 | B2 | 2/2010 | Libbus et al. |
| 7,664,548 | B2 | 2/2010 | Amurthur et al. |
| 7,668,602 | B2 | 2/2010 | Ben-David et al. |
| 7,672,733 | B2 | 3/2010 | Zhou et al. |
| 7,676,275 | B1 | 3/2010 | Farazi et al. |
| 7,684,866 | B2 | 3/2010 | Fowler et al. |
| 7,689,286 | B2 | 3/2010 | Pastore et al. |
| 7,711,415 | B1 | 5/2010 | Farazi et al. |
| 7,711,421 | B2 | 5/2010 | Shafer et al. |
| 7,734,355 | B2 | 6/2010 | Cohen et al. |
| 7,751,884 | B2 | 7/2010 | Ternes et al. |
| 7,769,442 | B2 | 8/2010 | Shafer |
| 7,769,446 | B2 | 8/2010 | Moffitt et al. |
| 7,778,702 | B2 | 8/2010 | Ben-David et al. |
| 7,778,703 | B2 | 8/2010 | Gross et al. |
| 7,778,711 | B2 | 8/2010 | Ben-David et al. |
| 7,783,353 | B2 | 8/2010 | Libbus et al. |
| 7,797,041 | B2 | 9/2010 | Libbus et al. |
| 7,801,603 | B2 | 9/2010 | Westlund et al. |
| 7,801,604 | B2 | 9/2010 | Brockway et al. |
| 7,801,614 | B2 | 9/2010 | Rossing et al. |
| 7,805,193 | B2 | 9/2010 | Libbus et al. |
| 7,805,203 | B2 | 9/2010 | Ben-David |
| 7,813,805 | B1 | 10/2010 | Farazi |
| 7,813,812 | B2 | 10/2010 | Kieval et al. |
| 7,835,797 | B2 | 11/2010 | Rossing et al. |
| 7,840,266 | B2 | 11/2010 | Libbus et al. |
| 7,840,271 | B2 | 11/2010 | Kieval et al. |
| 7,844,346 | B2 | 11/2010 | Cohen et al. |
| 7,848,812 | B2 | 12/2010 | Crowley et al. |
| 7,848,816 | B1 | 12/2010 | Wenzel et al. |
| 7,869,869 | B1 | 1/2011 | Farazi |
| 7,885,709 | B2 | 2/2011 | Ben-David |
| 7,885,711 | B2 | 2/2011 | Ben-Ezra et al. |
| 7,890,185 | B2 | 2/2011 | Cohen et al. |
| 7,894,907 | B2 | 2/2011 | Cowan et al. |
| 7,904,151 | B2 | 3/2011 | Ben-David |
| 7,904,175 | B2 | 3/2011 | Scott et al. |
| 7,904,176 | B2 | 3/2011 | Ben-Ezra et al. |
| 7,908,008 | B2 | 3/2011 | Ben-David et al. |

(56) References Cited

U.S. PATENT DOCUMENTS

| | | | |
|---|---|---|---|
| 7,916,013 B2 | 3/2011 | Stevenson | |
| 7,925,342 B2 | 4/2011 | Amurthur et al. | |
| 7,925,352 B2 | 4/2011 | Stack et al. | |
| 7,974,693 B2 | 7/2011 | Ben-David et al. | |
| 8,005,542 B2 | 8/2011 | Ben-Ezra et al. | |
| 8,005,545 B2 | 8/2011 | Ben-David et al. | |
| 8,036,745 B2 | 10/2011 | Ben-David et al. | |
| 8,060,197 B2 | 11/2011 | Ben-David et al. | |
| 8,065,021 B2 | 11/2011 | Gross et al. | |
| 8,083,663 B2 | 12/2011 | Gross et al. | |
| 8,116,881 B2 | 2/2012 | Cohen et al. | |
| 8,131,362 B2 | 3/2012 | Moffitt et al. | |
| 8,160,701 B2 | 4/2012 | Zhao et al. | |
| 8,160,705 B2 | 4/2012 | Stevenson et al. | |
| 8,195,290 B2 | 6/2012 | Brockway | |
| 8,224,436 B2 | 7/2012 | Libbus et al. | |
| 8,249,711 B2 | 8/2012 | Libbus et al. | |
| 8,369,943 B2 | 2/2013 | Shuros et al. | |
| 8,386,038 B2 | 2/2013 | Bianchi et al. | |
| 8,401,640 B2 | 3/2013 | Zhao et al. | |
| 8,417,354 B2 | 4/2013 | Zhang et al. | |
| 8,571,654 B2 | 10/2013 | Libbus et al. | |
| 8,577,458 B1 | 11/2013 | Libbus et al. | |
| 8,600,505 B2 | 12/2013 | Libbus et al. | |
| 8,634,921 B2 | 1/2014 | Chavan et al. | |
| 8,688,212 B2 | 4/2014 | Libbus et al. | |
| 2002/0107553 A1 | 8/2002 | Hill et al. | |
| 2003/0040774 A1 | 2/2003 | Terry et al. | |
| 2003/0153954 A1 | 8/2003 | Park et al. | |
| 2003/0171781 A1 | 9/2003 | Florio et al. | |
| 2004/0199210 A1* | 10/2004 | Shelchuk | A61N 1/36114 607/17 |
| 2004/0210261 A1 | 10/2004 | King et al. | |
| 2004/0215265 A1 | 10/2004 | Keizer | |
| 2005/0049655 A1 | 3/2005 | Boveja et al. | |
| 2005/0065553 A1 | 3/2005 | Ben-Ezra et al. | |
| 2005/0125044 A1 | 6/2005 | Tracey | |
| 2005/0131467 A1 | 6/2005 | Boveja | |
| 2005/0165465 A1 | 7/2005 | Pianca et al. | |
| 2005/0267542 A1 | 12/2005 | David et al. | |
| 2006/0015153 A1 | 1/2006 | Gliner et al. | |
| 2006/0100668 A1 | 5/2006 | Ben-David et al. | |
| 2006/0190053 A1 | 8/2006 | Dobak, III | |
| 2006/0206155 A1* | 9/2006 | Ben-David | A61N 1/0556 607/9 |
| 2006/0253161 A1 | 11/2006 | Libbus et al. | |
| 2007/0067004 A1 | 3/2007 | Boveja et al. | |
| 2007/0093870 A1 | 4/2007 | Maschino et al. | |
| 2007/0213773 A1 | 9/2007 | Hill et al. | |
| 2007/0233194 A1 | 10/2007 | Craig | |
| 2007/0255320 A1 | 11/2007 | Inman et al. | |
| 2007/0276453 A1 | 11/2007 | Hill et al. | |
| 2008/0015659 A1 | 1/2008 | Zhang et al. | |
| 2008/0021503 A1 | 1/2008 | Whitehurst et al. | |
| 2008/0033511 A1 | 2/2008 | Dobak | |
| 2008/0051839 A1 | 2/2008 | Libbus et al. | |
| 2008/0058874 A1* | 3/2008 | Westlund | A61B 5/1104 607/2 |
| 2008/0061240 A1 | 3/2008 | Heuft | |
| 2008/0091240 A1 | 4/2008 | Ben-David et al. | |
| 2008/0132983 A1 | 6/2008 | Cohen et al. | |
| 2008/0147140 A1 | 6/2008 | Ternes et al. | |
| 2008/0183258 A1 | 7/2008 | Inman | |
| 2008/0243196 A1 | 10/2008 | Libbus et al. | |
| 2008/0319513 A1 | 12/2008 | Pu et al. | |
| 2009/0030493 A1 | 1/2009 | Colburn et al. | |
| 2009/0118777 A1 | 5/2009 | Iki et al. | |
| 2009/0124848 A1 | 5/2009 | Miazga | |
| 2009/0149900 A1 | 6/2009 | Moffitt et al. | |
| 2009/0248097 A1 | 10/2009 | Tracey et al. | |
| 2009/0270953 A1 | 10/2009 | Ecker et al. | |
| 2009/0275956 A1 | 11/2009 | Burnes et al. | |
| 2010/0010556 A1 | 1/2010 | Zhao et al. | |
| 2010/0010603 A1 | 1/2010 | Ben-David et al. | |
| 2010/0016919 A1 | 1/2010 | Hill et al. | |
| 2010/0042173 A1 | 2/2010 | Farazi et al. | |
| 2010/0114197 A1 | 5/2010 | Burnes et al. | |
| 2010/0114203 A1 | 5/2010 | Burnes et al. | |
| 2010/0114227 A1 | 5/2010 | Cholette | |
| 2010/0174341 A1 | 7/2010 | Bolea et al. | |
| 2010/0286740 A1 | 11/2010 | Libbus et al. | |
| 2010/0331908 A1 | 12/2010 | Farazi | |
| 2011/0015692 A1 | 1/2011 | Libbus et al. | |
| 2011/0082514 A1 | 4/2011 | Libbus et al. | |
| 2011/0098796 A1 | 4/2011 | Ben-David et al. | |
| 2011/0224749 A1 | 9/2011 | Ben-David et al. | |
| 2011/0257708 A1 | 10/2011 | Kramer et al. | |
| 2011/0313488 A1 | 12/2011 | Hincapie Ordonez et al. | |
| 2012/0143286 A1 | 6/2012 | Hahn et al. | |
| 2012/0172742 A1 | 7/2012 | Arcot-Krishnamurthy et al. | |
| 2012/0185007 A1 | 7/2012 | Ziegler et al. | |
| 2012/0185010 A1 | 7/2012 | Zhou et al. | |
| 2012/0192874 A1 | 8/2012 | Bolea et al. | |
| 2012/0271374 A1 | 10/2012 | Nelson et al. | |
| 2012/0303080 A1 | 11/2012 | Ben-David et al. | |
| 2013/0158616 A1 | 6/2013 | Libbus et al. | |
| 2013/0158617 A1 | 6/2013 | Libbus et al. | |
| 2013/0158618 A1 | 6/2013 | Libbus et al. | |
| 2013/0238047 A1 | 9/2013 | Libbus et al. | |
| 2013/0289646 A1 | 10/2013 | Libbus et al. | |
| 2014/0025132 A1 | 1/2014 | Libbus et al. | |
| 2014/0135862 A1 | 5/2014 | Libbus et al. | |
| 2014/0135863 A1 | 5/2014 | Libbus et al. | |
| 2014/0135864 A1 | 5/2014 | Libbus et al. | |
| 2014/0228905 A1 | 8/2014 | Bolea | |
| 2014/0277232 A1 | 9/2014 | Libbus et al. | |
| 2015/0073511 A1 | 3/2015 | Libbus et al. | |
| 2015/0073512 A1 | 3/2015 | Libbus et al. | |
| 2015/0094962 A1 | 4/2015 | Hoegh et al. | |
| 2015/0119956 A1 | 4/2015 | Libbus et al. | |
| 2015/0196762 A1 | 7/2015 | Amurthur et al. | |

OTHER PUBLICATIONS

PCT Application No. PCT/US2012/068213, Search Report and Written Opinion dated Mar. 15, 2013, 11 pages.

PCT Application No. PCT/US2012/068223, Search Report and Written Opinion dated Apr. 3, 2013, 11 pages.

PCT Application No. PCT/US2013/021964, Search Report and Written Opinion dated Apr. 17, 2013, 10 pages.

PCT Application No. PCT/US2012/068211, Search Report and Written Opinion dated May 7, 2013, 9 pages.

PCT Application No. PCT/US2013/050390, Search Report and Written Opinion dated Nov. 5, 2013.

PCT Application No. PCT/US2013/068541, Search Report and Written Opinion dated Jan. 7, 2014.

PCT Application No. PCT/US2014/024827, Search Report and Written Opinion dated Nov. 11, 2014, 18 pages.

Abraham, et al., "Devices in the management of advanced, chronic heart failure," Nature Reviews, vol. 10, pp. 98-110 (Feb. 2013) (Published online Dec. 11, 2012).

Adamson, et al., "Continuous Autonomic Assessment in Patients with Symptomatic Heart Failure: Prognostic Value of Heart Rate Variability Measured by an Implanted Cardiac Resynchronization Device," Circulation, Journal of the American Heart Association, 110, pp. 2389-2394 (2004).

Agostoni, et al., "Functional and Histological Studies of the Vagus Nerve and its Branches to the Heart, Lungs and Abdominal Viscera in the Cat," J. Physiol. 135, pp. 182-205 (1957).

Ajani, et al., "Prevalence of High C-Reactive Protein in Persons with Serum Lipid Concentrations within Recommended Values," Chemical Chemistry, 50:9, pp. 1618-1622 (2004).

Akiyama, et al., "Effects of right and left vagal stimulation on left ventricular acetylcholine levels in the cat," Acta Physiol Scand, 172, pp. 11-16 (2001).

Anand, et al., "C-Reactive Protein in Heart Failure: Prognostic Value and the Effect of Valsartan," Circulation, Journal of the American Heart Association, 112, pp. 1428-1434 (2005).

Anholt, et al., "Recruitment and blocking properties of the CardioFit stimulation lead," Journal of Neural Engineering, 8, pp. 1-6, (2011).

(56) References Cited

OTHER PUBLICATIONS

Ardell, et al., "Selective vagal innervation of sinoatrial and atrioventricular nodes in canine heart," Am. J. Physiol. 251 (Heart Circ. Physiol. 20), pp. H764-H773 (1986).
Armour, "Cardiac neuronal herarchy in health and disease," Am J Physiol Regul Integr Comp Physiol, 287, pp. R262-R271 (2004).
Armour, "Myocardial ischaemia and the cardiac nervous system," Cardiovascular Research, 41, pp. 41-54 (1999).
Armour, JA, "Potential clinical relevance of the 'little brain' on the mammalian heart," Experimental Physiology, vol. 1 93, No. 2, pp. 165-176 (Feb. 2008). Online Publication Date: Nov 2, 2007. Available at: http://ep.physoc.org/ content/93/2/165.long.
Armour, "The little brain on the heart," Cleveland Clinic Journal of Medicine, vol. 74, supp. 1, pp. S48-S51 (Feb. 2007).
Armour, et al., "Functional anatomy of canine cardiac nerves," Acta anat., 91, pp. 510-528 (1975).
Armour, et al., "Localized myocardial responses to stimulation of small cardiac branches of the vagus," American Journal of Physiology, vol. 228, No. 1 pp. 141-148 (Jan. 1975).
Asala, et al., "An electron microscope study of vagus nerve composition in the ferret," Anat Embryol, 175, pp. 247-253 (1986).
Aukrust, et al., "Inflammatory and anti-inflammatory cytokines in chronic heart failure: Potential therapeutic implications," Annals of Medicine, 37, pp. 74-85 (2005).
Author Unknown, "Nerve fiber—Types and Function," www.boddunan.com Available at ww.boddunan.com/education/20-medicine-a-surgery/12730-nerver-fiber-types-and-function.html (Apr. 19, 2010).
Author Unknown, American Diabetes Association, "Standards of Medical Care in Diabetes—2012," Diabetes Care, vol. 35, supplement 1, pp. S11-S63 (Jan. 2012).
Author Unknown, Staff of Adinstruments, "Principles of Nerve Stimulation," Application Note, ADInstruments (Apr. 2002).
Bae, et al., "Gliosis in the Amygdala Following Myocardial Infarction in the Rat," J Vet Med Sci, 72(8), pp. 1041-1045 (2010).
Bernik, et al., "Pharmacological Stimulation of the Cholinergic Antiinflammatory Pathway," J. Exp. Med, vol. 195, No. 6, pp. 781-788 (Mar. 18, 2002).
Berthoud, et al., "Functional and chemical anatomy of the afferent vagal system," Autonomic Neuroscience: Basic and Clinical, 85, pp. 1-17 (2000).
Bhagat, et al., "Differential Effect of Right and Left Vagal Stimulation on Right and Left Circumflex Coronary Arteries," S A Medical Journal, 50, pp. 1591-1594 (1976).
Biasucci, et al., "Elevated Levels of C-Reactive Protein at Discharge in Patients with Unstable Angina Predict Recurrent Instability," Circulation,Journal of the American Heart Association, 99, pp. 855-860 (1999).
Bibevski, et al., "Evidence for impaired vagus nerve activity in heart failure," Heart Fail Rev, 16, pp. 129-135 (2011).
Bibevski, et al., "Ganglionic Mechanisms Contribute to Diminished Vagal Control in Heart Failure," Circulation, Journal of the American Heart Association, 99, pp. 2958-2963 (1999).
Bilgutay, et al., "Vagal Tuning a new concept in the treatment of supraventricular arrhythmias, angina pectoris, and heart failure," Journal of Thoracic and Cardiovascular Surgery, vol. 56, No. 1, pp. 71-82 (Jul. 1968).
Binkley, et al., "Parasympathetic Withdrawal Is an Integral Component of Autonomic Imbalance in Congestive Heart Failure: Demonstration in Human Subjects and Verification in a Paced Canine Model of Ventricular Failure,"JACC, vol. 18, No. 2, pp. 464-472 (Aug. 1991).
Bois, et al., "Mode of action of bradycardic agent, S 16257, on ionic currents of rabbit sinoatrial node cells," Abstract, British Journal of Pharmacology, 118(4):1051-7 (1996).
Bonaz, et al., "Vagus nerve stimulation: From epilepsy to the cholinergic anti-inflammatory pathway," Neurogastroenterology & Motility, pp. 1-14 (2013).
Borggrefe, et al., "Vagal Stimulation Devices," ESC Congress 2010 (2010).

Borovilkova, et al., "Vagus nerve stimulation attenuates the systemic inflammatory response to endotoxin," Nature, vol. 405, pp. 458-462 (May 25, 2000).
Brack, et al., "Mechanisms underlying the autonomic modulation of ventricular fibrillation initiation—tentative prophylactic properties in vagus nerve stimulation on malignant arrhythmias in heart failure," Heart Fail Rev (Published online Jun. 8, 2012).
Bronzino, "Biomedical Engineering Fundamentals," CRC Press, Chapter 30, pp. 30-10-30-15 (Apr. 2006).
Buschman, et al., "Heart Rate Control Via Vagus Nerve Stimulation," Neuromodulation, vol. 9, No. 3, pp. 214-220 (2006).
Butterwick, et al., "Tissue Damage by Pulsed Electrical Stimulation," IEEE Transactions on Biomedical Engineering, vol. 54, No. 12, pp. 2261-2267 (Dec. 2007).
Calkins, et al., "Comparison of Responses to Isoproterenol and Epinephrine During Head-Up Tilt in Suspected Vasodepressor Syncope," The American Journal of Cardiology, vol. 67 pp. 207-209 (Jan. 15, 1991).
Castoro, et al., "Excitation properties of the right cervical vagus nerve in adult dogs," Experimental Neurology, 227 (pp. 62-68 (2011).
Chapleau, et al., "Methods of assessing vagus nerve activity and reflexes," Heart Fail Rev, 16, pp. 109-127 (2011).
Chen, et al., "National and Regional Trends in Heart Failure Hospitalization and Mortality Rates for Medicare Beneficiaries, 1998-2008," JAMA, vol. 306, No. 15 (Oct. 19, 2011).
Chen, et al., "Role of Atrial Electrophysiology and Autonomic Nervous System in Patients with Supraventricular Tachycardia and Paroxysmal Artrial Fibrillation," J Am Coll Cardiol, vol. 32, No. 3, pp. 732-738 (Sep. 1998).
Cheng, et al., "Long-term Outcomes in Individuals with Prolonged PR Interval or First-Degree Atrioventricular Block," JAMA, vol. 301, No. 24 pp. 2571-2577 (Jun. 24, 2009).
Chiou, et al., "Effects of Continuous Enhanced Vagal Tone and Dual Atrioventricular Node and Accessory Pathways," Circulation, Journal of the American Heart Association, 107, pp. 2583-2588 (2003).
Cohen, et al., "Histopathology of the stimulated Vagus nerve: Primum non nocere," Heart Fail Rev, 16, pp. 163-169 (2011).
Colombo, et al., "Comparison between spectral analysis and the phenylephrine methods for the assessment of baroreflex sensitivity in chronic heart failure," Clinical Science, 97, pp. 503-513 (1999).
Cryan, et al., "Animal models and mood disorders: recent developments," Current Opinion in Psychiatry, 20, pp. 1-7 (2007).
Das, "Vagal nerve stimulation in prevention and management of coronary heart disease," World J. Cardiol, 3(4), pp. 105-110 (Apr. 26, 2011).
De Castro, et al., "Parasympathetic-mediated atrial fibrillation during tilt test associated with increased baroreflex sensitivity," The European Society of Cardiology, Europace, 8, pp. 349-351 (2006).
De Ferrari, et al., "Baroreflex Sensitivity Predicts Long-Term Cardiovascular Mortality After Myocardial Infarction Even in Patients with Preserved Left Ventricular Function," Journal of the American College of Cardiology, vol. 50, No. 24, pp. 2285-2290 (2007).
De Ferrari, et al., "Chronic Vagal Stimulation in Patients with Congestive Heart Failure," 31st Annual International Conference of the IEE EMBS (2009).
De Ferrari, et al., "Chronic vagus nerve stimulation: a new and promising therapeutic approach for chronic heart failure," European Heart Journal, 32, pp. 847-855 (2011).
De Ferrari, et al., "Vagus nerve stimulation: from pre-clinical to clinical application: challenges and future directions," Heart Fail Rev, 16, pp. 195-203 (2011) (Published Online Dec. 17, 2010).
De Jonge, et al., "Stimulation of the vagus nerve attenuates macrophage activation by activating the Jak2-STAT3 signaling pathway," Nature Immunology, vol. 6, No. 8, pp. 844-852 (Aug. 2005).
Desai, et al., "Pharmacologic modulation of parasympathetic activity in heart failure," Heart Fail Rev, 16, pp. 179-193 (Published online: Oct. 6, 2010) (2011).
Dickerson, et al., "Parasympathetic neurons in the cranial medial ventricular fat pad on the dog heart selectively decrease ventricular contractility," Journal of the Autonomic Nervous System, 70, pp. 129-141 (1998).

(56) References Cited

OTHER PUBLICATIONS

Dunlap, et al., "Mechanisms of altered vagal control in heart failure: influence of muscarinic receptors and acetylcholinesterase activity," Am J Physiol Heart Circ Physiol, 285, pp. H1632-H1640 (Jun. 26, 2003).
Elsenbruch, et al., "Heart Rate Variability During Waking and Sleep in Healthy Males and Females," SLEEP, vol. 22, No. 8, pp. 1067-1071 (1999).
Euler, et al., "Acetylcholine release by a stimulus train lowers atrial fibrillation threshold," Am. J Physiol. 253 (Heart Circ. Physiol, 22), pp. H863-H868 (1987).
Evans, et al., "Histological and functional studies on the fibre composition of the vagus nerve of the rabbit," Journal of Anatomy, 130, pp. 139-151 (1954).
Fallen, "Vagal Afferent Stimulation as a Cardioprotective Strategy? Introducing the Concept," A.N. E., vol. 10, No. 4 (Oct. 2005).
Fan, et al., "Transvenous vagus nerve stimulation: A potential heart failure therapy is feasible in humans," JACC, vol. 55, issue 10A, pp. E152-E153 (2010).
Fazan, et al., "Diabetic Peripheral Neuropathies: A Morphometric Overview," Int. J. Morphol, 28(I), pp. 51-64 (2010).
Feinauer, et al., "Ouabain enhances release of acetylcholine in the heart evoked by unilateral vagal stimulation," Arch Pharmacol, 333, pp. 7-12 (1986).
Fonarow, et al., "Incremental Reduction in Risk of Death Associated with Use of Gudeline-Recommended Therapies in Patients with Heart Failure: A Nested Case-Control Analysis of Improve HF," J Am Heart Assoc, 1, pp. 16-26 (2012).
Ford, et al., "The effects of electrical stimulation of myelinated and non-myelinated vagal fibres on heart rate in the rabbit," J. Physiol. 380, pp. 341-347 (1986).
Furukawa, et al., "Effects of Verapamil, Zatebradine, and E-4031 on the Pacemaker Location and Rate in Response to Sympathetic Stimulation in Dog Hearts," The Journal of Pharmacology and Experimental Therapeutics, vol. 289, No. 3, pp. 1334-1342 (1999).
Furukawa, et al., "Selective inhibition by zatebradine and discrete parasympathetic stimulation of the positive chronotropic response to sympathetic stimulation in anesthetized dogs," Abstract, Journal of Pharmacology & Experimental Therapeutics, 272(2):744-9 (1995).
Gatti, et al., "Can neurons in the nucleus ambiguus selectively regulate cardiac rate and atrio-ventricular conduction?" Journal of the Autonomic Nervous System, 57, pp. 123-127 (1996).
Gatti, et al., "Vagal control of left ventricular contractility is selectively mediated by a cranioventricular intracardiac ganglion in the cat," Journal of the Autonomic Nervous System, 66, pp. 138-144 (1997).
Gibbons, et al., "Neuromodulation targets intrinsic cardiac neurons to attenuate neuronally mediated atrial arrhythmias," Am J Physiol Regul Integr Comp Physiol 302: R357-R364 (2012) (First published Nov. 16, 2011).
Gottdiener, et al., "Predictors of Congestive Heart Failure in the Elderly: The Cardiovascular Heatlh Study," Journal of the American College of Cardiology, vol. 35, No. 6, pp. 1628-1637 (2000).
Gray, et al., "Parasympathetic control of the Heart. II. A novel interganglionic intrinsic cardiac circuit mediates neural control of heart rate," J. Appl Physiol, 96, pp. 2273-2278 (2004).
Gray, et al., "Parasympathetic control of the Heart. III. Neuropeptide Y-immunoreactive nerve terminals synapse on three populations of negative chronotropic vagal preganglionic neurons," J. Appl Physiol, 96, pp. 2279-2287 (2004).
Grill, "Chapter 14—Principles of Electric Field Generation for Stimulation of the Central Nervous System," Neuromodulation, Academic Press (2009).
Guilleminault, et al., "Cyclical Variation of the Heart Rate in Sleep Apnoea Syndrome," The Lancet, pp. 126-131 (Jan. 21, 1984).
Hardwick, et al., "Chronic myocardial infarction induces phenotypic and functional remodeling in the guinea pig cardiac plexus," Am J Physiol Regulatory Integrative Comp Physiol, 295, pp. 1926-1933 (2008).
Hardwick, et al., "Remodeling of the guinea pig intrinsic cardiac plexus with chronic pressure overload," Am J Physiol Regulatory Integrative Comp Physiol, 297, pp. 859-866 (2009).
Hauptman, et al., "The vagus nerve and autonomic imbalance in heart failure: past, present, and future," Heart Fail Rev, 16, pp. 97-99 (2011).
Hellyer, et al., "Autonomic nerve activity and blood pressure in ambulatory dogs," Heart Rhythym, vol. 11(2), pp. 307-313 (Feb. 2014).
Hirooka, et al., "Imbalance of central nitric oxide and reactive oxygen species in the regulation of sympathetic activity and neural mechanisms of hypertension," Am J Physiol Regulatory Integration Comp Physiol, 300, pp. 818-826 (2011).
Hoffman, et al., "Vagus Nerve Components," Anat Rec, 127, pp. 551-568 (1957).
Hu, et al., "Role of sympathetic nervous system in myocardial ischemia injury: Beneficial or deleterious?" Letters to the Editor, Elsevier Ireland Ltd. (Mar. 27, 2012).
Hua, et al., "Left vagal stimulation induces dynorphin release and suppresses substance P release from the rat thoracic spinal cord during cardiac ischemia," Am J Physiol Regulatory Integration Comp Physiol, 287, pp. 1468-1477 (2004).
Huston, et al., "Splenectomy inactivates the cholinergic antiinflammatory pathway during lethal endotoxemia and polymicrobial sepsis," J. Exp. Med, vol. 203, No. 7 pp. 1623-1628 (Jun. 19, 2006).
Huston, et al., "Transcutaneous vagus nerve stimulation reduces serum high mobility group box 1 levels and improves survival in murine sepsis," Crit Care Med, vol. 35, No. 12, pp. 2762-2768 (2007).
Ingemansson, et al., "Autonomic modulation of the atrial cycle length by the head up tilt test: non-invasive evaluation in patients with chronic atrial fibrillation," Heart, 80, pp. 71-76 (1998).
Ito, et al., "Efferent sympathetic and vagal innervation of the canine right ventricle," Circulation, Journal of the American Heart Association, vol. 90, pp. 1469-1468 (1994).
Jacques, et al., "Spinal Cord Stimulation Causes Potentiation of Right Vagus Nerve Effects on Atrial Chronotropic Function and Repolarization in Canines," Journal of Cardiovascular Electrophysiology, vol. 22, No. 4, pp. 440-447 (Apr. 2011).
Jaenisch, et al., "Respiratory muscle training improves baroreceptor sensitivity, decrease sympathetic tonus and increase vagal effect in rats with heart failure," European Heart Journal, 32 (Abstract Supplement, pp. 976 (2011).
Jammes, et al., "Afferent and efferent components of the bronchial vagal branches in cats," Journal of the Autonomic Nervous System, 5, pp. 165-176 (1982).
Janabi, et al., "Oxidized LDL—Induced NF-kB Activation and Subsequent Expression of Proinflammatory Genes are Defective in Monocyte-Derived Macrophages from CD36-Deficient Patients," Arterioscler Thromb Vasc Biol., 20:1953-1960 (2000).
Janse, et al., "Effects of unilateral stellate ganglion stimulation and ablation on electrophysiologic changes induced by acute myocardial ischemia in dogs," Circulation, Journal of the American Heart Association, 72, pp. 585-595 (1985).
Jessup, et al., "2009 Focused Update: ACCF/AHA Guidelines for the Diagnosis and Management of Heart Failure in Adults," Circulation, Journal of the American Heart Association, vol. 119, pp. 1977-2016 (2009).
Johnson, et al., "Parasympathetic control of the heart. I. An interventriculo-septal ganglion is the major source of the vagal intracardiac innervation of the ventricles," J Appl Physiol, 96, pp. 2265-2272 (2004).
Kakinuma, et al., "Cholinoceptive and cholinergic properties of cardiomyocytes involving an amplification mechanism for vagal efferent effects in sparsely innervated ventricular myocardium," FEBS Journal, 276, pp. 5111-5125 (2009).
Kalman, "Specific effects of zatebradine on sinus node function: suppression of automaticity, prolongation of sinoatrial conduction and pacemaker shift in the denervated canine heart," Abstract, Journal of Pharmacology & Experimental Therapeutics, 272(1):85-93 (1995).
Kaneko, et al., "C-Reactive Protein in Dilated Cardiomyopathy," Cardiology, 91, pp. 215-219 (1999).

(56) References Cited

OTHER PUBLICATIONS

Katare, et al., "Vagal nerve stimulation prevents reperfusion injury through inhibition of opening of mitochondrial permeability transition pore independent of bradycardiac effect," The Journal of Thoracic and Cardiovascular Surgery, vol. 137, No. 1, pp. 223-231 (2009).

Katz, et al., "Diseases of the heart in the Works of Hippocrates," Br Heart J, 24, pp. 257-264 (1962).

Kawada, et al., "High-frequency dominant depression of peripheral vagal control of heart rate in rats with chronic heart failure," Acta Physiol 207, 494-502 (2013).

Kawada, et al., "Vagal stimulation suppresses isschemia-induced myocardial interstitial norepinephrine release," Life Sciences, 78, pp. 882-887 (2006).

Kawashima, "The autonomic nervous system of the human heart with special reference to its origin, course, and peripheral distribution," Anat Embryol, 209, pp. 425-438 (2005).

Klein et al., "Vagus nerve stimulation: A new approach to reduce heart failure," Cardiology Journal, vol. 17, iss. 6, pp. 638-643 (2010).

Kliks, et al., "Influence of Sympathetic Tone on Ventricular Fibrillation Threshold During Experimental Coronary Occlusion," The American Journal of Cardiology, vol. 36, pp. 45-49 (Jul. 1975).

Kolman, et al., "The effect of vagus nerve stimulation upon vulnerability of the canine ventricle: role of sympathetic-parasympathetic interactions," Journal of the American Heart Association, 52, pp. 578-585 (1975).

Kong, et al., "Optimizing the Parameters of Vagus Nerve Stimulation by Uniform Design in Rats with Acute Myocardial Infarction," PLOS One, vol. 7, issue 11 (Nov. 2012).

Koopman, et al., "Pilot study of stimulation of the cholinergic anti-inflammatory pathway with an implantable vagus nerve stimulation device in patients with rheumatoid arthritis," Abstract (2012).

Kulbertus, et al., ed., "Neurocardiology," Futura Publishing Co., pp. 13 ("Anatomy of the Cardiac Efferent Innvervation"); 61-63 ("Autonomic Neural Control"); 87, 89, 92-93 ("Sympathetic-Parasympathetic Interactions"); 183, 187 ("Parasympathetic Nervous System"); 104 (1988).

La Rovere, et al., "Baroreflex Sensitivity and Heart Rate Variability in the Identification of Patients at Risk for Life-Threatening Arrhythmias: Implications for Clinical Trials," Circulation, Journal of the American Heart Association, 103, pp. 2072-2077 (2011).

La Rovere, et al., "Baroreflex sensitivity and heart-rate variability in prediction of total cardiac mortality after myocardial infarction. ATRAMI (Autonomic Tone and Reflexes After Myocardial Infarction) Investigators," Lancet, 351(9101), pp. 478-484 (Feb. 14, 1998).

Lane, et al., "Prediction and Prevention of Sudden Cardiac Death in Heart Failure," Heart, 91, pp. 674-680 (2005).

Lechat, et al., "Heart rate and Cardiac Rhythm Relationships with Bisoprolol Benefit in Chronic Heart Failure in CIBIS II Trial," Circulation, Journal of American Heart Association, 103, pp. 1428-1433 (2001).

Lewis, et al., "Vagus nerve stimulation decreases left ventricular contractility in vivo in the human and pig heart," Journal of Physiology, 534, pp. 547-552 (2001).

Li, et al., "Early vagal stimulation markedly prevented cardiac dysfunction in rats after acute myocardial infarction in addition to suppressing arrhythmic death," European Heart Journal, 32 (Abstract Supplement), pp. 297-298 (2011).

Li, et al., "Inflammatory cytokines and nitric oxide in heart failure and potential modulation by vagus nerve stimulation," Heart Fail Rev, 16, pp. 137-145 (2011).

Li, et al., "Low-Level Vagosympathetic Stimulation. A Paradox and Potential New Modality for the Treatment of Focal Atrial Fibrillation," Circ Arrhythm Electrophysiol, Journal of American Heart Association, 2, pp. 645-651 (2009).

Li, et al., "Restoration of vagal tone by donepezil, on top of losartan treatment, markedly suppresses ventricular dysfunction and improves long-term survival in chronic heart failure rats," European Heart Journal, 32 (Abstract Supplement), pp. 642 (2011).

Li et al., "Vagal Nerve Stimulation Markedly Improves Long-Term Survival After Chronic Heart Failure in Rats," Circulation: Journal of the American Heart Association, vol. 109, iss. 1, pp. 120-124 (Jan. 2004). Online publication date: Dec. 8, 2003.

Libby, et al., "Inflammation and Atherosclerosis," Circulation, Journal of the American Heart Association, 105, pp. 1135-1143 (2002).

Liu, et al., "Differing sympathetic and vagal effects on atrial fibrillation in dogs: role of refractoriness heterogeneity,"Am. J. Physiol. 273 (Heart Circ. Physiol. 42), pp. H805-H816 (1997).

Lo, et al., "Paradoxical long-term proarrhythmic effects after ablating the 'head station' ganglionated plexi of the vagal innervation to the heart," Heart Rhythm, vol. 10, No. 5, pp. 751-757 (May 2013).

Lohmeier, et al., "Prolonged Activation of the Barorelfex Produces Sustained Hypotension," Hypertension, Journal of the American Heart Association, 43, pp. 306-311 (2004).

Lu, et al., "Vagal nerve stimulation protects cardiac injury by attenuating mitochondrial dysfunction in a murine burn injury model," J. Cell. Mol. Med., vol. 17, No. 5, pp. 664-671 (2013).

Ma, et al., "Analysis of afferent, central, and efferent components of the baroreceptor reflex in mice," Am J Physiol Regulatory Integration Comp Physiol, 283, pp. 1033-1040 (2002).

Maj, et al., "P5775: Autonomic imbalance and circulating androgens and estrogens in men with systolic heart failure," European Heart Journal, 32 (Abstract Supplement), pp. 1090 (2011).

Malkin, et al., "Life-saving or life-prolonging? Interpreting trial data and survival curves for patients with congestive heart failure," The European Journal of Heart Failure, 7, pp. 143-148 (2005).

Mann, "Chapter 12—Peripheral Nerves," The Nervous System in Action, michaeldmann.net/mannl2.html, (Jul. 2011).

Mann, "Inflammatory Mediators and the Failing Heart. Past, Present, and the Foreseeable Future," Circ Res., 91, pp. 988-998 (2002).

Mann, "Stress-Activated Cytokines and the Heart: From Adaptation to Maladaptation," Annu. Rev. Physiol., 65, pp. 81-101 (2003).

Martin-Portugues, et al., "Histopathologic features of the vagus nerve after electrical stimulation in swine," Histol Histopathol, 20, pp. 851-856 (2005).

Martins, et al., "Distribution of Local Repolarization Changes Produced by Efferent Vagal Stimulation in the Canine Ventricles," JACC, vol. 2, No. 6, pp. 1191-1199 (Dec. 1983).

Massari, et al., "Neural control of left ventricular contractility in the dog heart: synaptic interactions of negative inotropic vagal preganglionic neurons in the nucleus ambiguus and tyrosine hydroxylase immunoreactive terminals," Brain Research, 802, pp. 205-220 (1998).

May, et al., "P564: Long-term prediction of all-cause mortality in diabetic autonomic neuropathy: simple function tests or 24-hour heart rate variability (HRV)?" European Heart Journal, 32 (Abstract Supplement, pp. 64 (2011).

Mei, et al., "The Composition of the Vagus Nerve of the Cat," Cell Tissue Res., 209, pp. 423-431 (1980).

Merrill, et al., "Electrical stimulation of excitable tissue: design of efficacious and safe protocols," Journal of Neuroscience Methods, 141, pp. 171-198 (2005).

Mortara, et al., "Arterial Baroreflex Modulation of Heart Rate in Chronic Heart Failure," Circulation, Journal of the American Heart Association, vol. 96, No. 10, pp. 3450-3458 (Nov. 18, 1997).

Murakawa, et al., "Effect of Cervical Vagal Nerve Stimulation on Defibrillation Energy," Jpn Heart J, 44, pp. 91-100 (Jan. 2003).

Naito, "Effects of zatebradine and propranolol on canine ischemia and reperfusion-induced arrhythmias," European Journal of Pharmacology, 388, pp. 171-176 (2000).

Nakajima, et al., "Autonomic Control of the Location and Rate of the Cardiac Pacemaker in the Sinoatrial Fat Pad of Parasympathetically Denervated Dog Hearts," Journal of Cardiovascular Electrophysiology, vol. 13, No. 9 pp. 896-901 (Sep. 2002).

Nearing, et al., "Crescendo in Depolarization and Repolarization Heterogeneity Heralds Development of Ventricular Tachycardia in Hospitalized Patients with Decompensated Heart Failure," Circulation Arrhythmia and Electrophysiology, Journal of the American Heart Association, 5, pp. 84-90 (2012).

(56) References Cited

OTHER PUBLICATIONS

Nihei, et al., "Decreased Vagal Control Over Heart Rate in Rats with Right-Sided Congestive Heart Failure—Downregulation of Neuronal Nitric Oxide Synthase," Circ J, 69, pp. 493-499 (2005).
Ninomiya, "Direct Evidence of Nonuniform Distribution of Vagal Effects on Dog Atria," Circulation Research, vol. XIX, pp. 576-583 (Sep. 1966).
Nolan, et al., "Prospective Study of Heart Rate Variability and Mortality in Chronic Heart Failure: Results of the United Kingdom Heart Failure Evaluation and Assessment of Risk Trial (UK-Heart)," Circulation, Journal of the American Heart Association, 98, pp. 1510-1516 (1998).
Ochoa, et al., "P2497: Effects of insulin resistance on resting heart rate, baroreflex sensitivity and indices of autonomic cardiovascular modulation in individuals with high blood pressure levels," European Heart Journal, 32 (Abstract Supplement, pp. 431-432 (2011).
Ogawa, et al., "Left Stellate Ganglion and Vagal Nerve Activity and Cardiac Arrhythmias in Ambulatory Dogs with Pacing-Induced Congestive Heart Failure," Journal of the American College of Cardiology, vol. 50, No. 4, pp. 335-444 (2007).
Okada, et al., "Cyclic Stretch Upregulates Production of Interleukin-8 and Monocyte Chemotactic and Activating Factor/Monocyte Chemoattractant Protein-1 in Human Endothelial Cells," Arterioscler Thromb Vasc Biol., 18, pp. 894-901 (1998).
Oliveira, et al., "Effects of vagal stimulation on induction and termination of atrial fibrillation in an in vivo rabbit heart model," Rev Port Cardiol, 29(03), pp. 375-389 (2010).
Olshansky, et al., "Parasympathetic Nervous System and Heart Failure: Pathophysiology and Potential Implications for Therapy," Circulation, Journal of the American Heart Association, 118, pp. 863-871 (2008).
Onkka, et al., "Sympathetic nerve fibers and ganglia in canine cervical vagus nerves: Localization and quantitation," Heart Rhythm, vol. 10, No. 4, pp. 585-591 (Apr. 2013).
Ordelman, et al., "Selectivity for Specific Cardiovascular Effects of Vagal Nerve Stimulation with a Multi-Contact Electrode Cuff," IEEE, pp. 1-6 (2011).
Packer, et al., "Effect of Carvedilol on Survival in Severe Chronic Heart Failure," The New England Journal of Medicine, vol. 344, No. 22, pp. 1651-1658 (May 31, 2001).
Pavlov, et al., "Central muscarinic cholinergic regulation of the systemic inflammatory response during endotoxemia," PNAS, vol. 103, No. 13, pp. 5219-5223 (Mar. 28, 2006).
Pavlov, et al., "Controlling inflammation: the cholinergic anti-inflammatory pathway," Biochemical Society Transactions, vol. 34, part 6, pp. 1037-1040 (2006).
Peckham, et al., "Chapter 18—Implantable Neural Stimulators," Neuromodulation, Academic Press (2009).
Pina, et al., "The Predictive Value of Biomarkers in Heart Failure," Medscape Education Cardiology, Available at http://www.medscape.org/viewarticle/765328 (CME Released: Jun. 15, 2012).
Pitzalis, et al., "Comparison Between Noninvasive Indices of Baroreceptor Sensitivity and the Phenylephrine Method in Post-Myocardial Infarction Patients," Circulation, Journal of the American Heart Association, 97, pp. 1362-1367 (1998).
Poole-Wilson, "Relation of Pathophysiologic Mechanisms to Outcome in Heart Failure," JACC, vol. 22, No. 4 (supplement A), pp. 22A-29A (Oct. 1993).
Pye, et al., "Study of serum C-reactive protein concentration in cardiac failure," Br Heart J, 63, pp. 228-230 (1990).
Rademacher, et al., "P5878: Multidimensional holter-based analysis of cardiac autonomic regulation predicts early AF recurrence after electrical cardioversion," European Heart Journal, 32 (Abstract Supplement), pp. 1116-1117 (2011).
Randall, et al., "Regional vagosympathetic control of the heart," American Journal of Physiology, vol. 227, No. 2, pp. 444-452 (1974).
Randall, et al., "Selective Vagal Innervation of the Heart," Annals of Clinical and Laboratory Science, vol. 16, No. 3, pp. 198-208 (1986).
Raymond, et al., "Elevated interleukin-6 levels in patients with asymptomatic left ventricular systolic dysfunction," American Heart Journal, vol. 141, No. 3, pp. 435-438 (Mar. 2001).
Rhee, et al., "Effects of suprathreshold vagal stimulation on stellate ganglion nerve activity in ambulatory dogs," 33rd Annual Scientific Sessions, Heart Rhythm, Presentation Abstract (2012).
Riccio, et al., "Interganglionic segregation of distinct vagal afferent fibre phenotypes in guinea-pig airways," Journal of Physiology, 495.2, pp. 521-530 (1996).
Riddle, et al., "Epidemiologic Relationships Between A1C and All-Cause Mortality During a Median 3.4-Year Follow-up of Glycemic Treatment in the ACCORD Trial," Diabetes Care, vol. 33, No. 5, pp. 983-990 (May 2010).
Ridker, "C-Reactive Protein: A Simple Test to Help Predict Risk of Heart Attack and Stroke," Journal of the American Heart Association, 108, pp. e81-e85 (2003).
Ridker, et al., "Comparison of C-Reactive Protein and Low-Density Lipoprotein Cholesterol Levels in the Prediction of First Cardiovascular Events," New England Journal of Medicine, vol. 347, No. 20, pp. 1557-1566 (Nov. 14, 2002).
Ridker, et al., "C-Reactive Protein and Other Markers of Inflammation in the Prediction of Cardiovascular Disease in Women," The New England Journal of Medicine, vol. 342, No. 12, pp. 836-841 (Mar. 23, 2000).
Ridker, et al., "Inflammation, Pravastatin, and the Risk of Coronary Events After Myocardial Infarction in Patients With Average Cholesterol Levels," Circulation, Journal of the American Heart Association, 98, pp. 839-844 (1998).
Roger, et al., "Heart Disease and Stroke Statistics-2011 Update: A Report from the American Heart Association," Circulation, Journal of the American Heart Association. Available at http://circ.ahajournals.org/content/123/4/e18 (2010).
Romanovsky, et al., "The vagus nerve in the thermoregulatory response to systemic inflammation," Am. J. Physiol., 273, pp. R407-R413 (1997).
Rossi, et al., "Epicardial ganglionated plexus stimulation decreases postoperative inflammatory response in humans," Heart Rhythm, vol. 9, No. 6, pp. 943-950 (Jun. 2012).
Rouse, et al., "The haemodynamic actions of ZENCA ZD7288, a novel sino-atrial node function modulator, in the exercising beagle: a comparison with zategradine and propranolol," Abstract, British Journal of Pharmacology, 113(3):1071-7 (1994).
Rozman, et al., "Heart function influenced by selective mid-cervical left vagus nerve stimulation in a human case study," Hypertension Research, 32, pp. 1041-1043 (2009).
Rutecki, "Anatomical, Physiological and Theoretical Basis for the Antiepileptic Effect of Vagus Nerve Stimulation," Epilepsia, 31 (suppl. 2), pp. S1-S6 (1990).
Sabbah, et al., "3722: Vagus nerve stimulation improves left ventricular function in heart failure: results of a 6 month investigation with a cross-over design in dogs with experimental heart failure," European Heart Journal, 32 (Abstract Supplement), pp. 642 (2011).
Sabbah, et al., "Baroreflex Activation Therapy for the Treatment of Heart Failure," Presentation available at http://www.cvrx.com/wp/wp-content/uploads/2012/04/Dr.-Sabbah-Slides.pdf (2012).
Sabbah, et al., "Chronic Electrical Stimulation of the Carotid Sinus Baroreflex Improves Left Ventricular Function and Promotes Reversal of Ventricular Remodeling in Dogs with Advanced Heart Failure," Circulation Heart Failure, Journal of the American Heart Association, 4, pp. 65-70 (2011).
Sabbah et al., "Vagus nerve stimulation in experimental heart failure," Heart Failure Reviews, vol. 16, No. 2, pp. 171-178 (Mar. 2011). Online Publication Date: Dec. 3, 2010.
Samara, et al., "The Effects of Cardiac Resyhchronization Therapy on Chronotropic Incompetence in Patients Intolerant of Beta Antagonist Therapy," Journal of Cardiac Failure, vol. 17, No. 8S, pp. S-54-S55 (Aug. 2011).
Sanner, et al., "P4743: Prediction of cardiovascular risk from nocturnal pulse wave signal using the autonomic state indicator (ASI) technology," European Heart Journal, 32 (Abstract Supplement), pp. 839 (2011).

(56) References Cited

OTHER PUBLICATIONS

Sato, et al., "Serial Circulating Concentrations of C-Reactive Protein, Interleukin (IL)-4, and IL-6 in Patients with Acute Left Heart Decompensation," Clin. Cardiol. 22, pp. 811-813 (1999).
Schauerte, "Time for Change: Cardiac neurophysiology meets cardiac electrophysiology," Editorial Commentary, Heart Rhythm Society (2013).
Schiereck, et al., "AV blocking due to asynchronous vagal stimulation in rats," Am J Physiol Heart Circ Physiol, 278, pp. H67-H73 (2000).
Schocken, et al., "Prevalence and Mortality Rate of Congestive Heart Failure in the United States," JACC, vol. 20, No. 2, pp. 301-6 (Aug. 1992).
Schwartz, "Vagal Stimulation for Heart Diseases: From Animals to Men," Circulation Journal, vol. 75, pp. 20-27 (Jan. 2011).
Schwartz, "Vagal stimulation for heart failure," Current Opinion in Cardiology, 26, pp. 51-54 (2011).
Schwartz, "Vagal stimulation for the treatment of heart failure: a translational success story," Heart, vol. 98, No. 23, pp. 1687-1690 (2012).
Schwartz, et al. Vagal stimulation for heart failure: Background and first in-man study, Heart Rhythm, 6, 11 suppl., pp. S76-S81 (Nov. 2009).
Schwartz, et al., "Autonomic mechanisms and sudden death. New insights from analysis of baroreceptor reflexes in conscious dogs with and without myocardial infarction," Circulation, Journal of the American Heart Association, 78, pp. 969-979 (1988).
Schwartz, et al., "Effects of Unilateral Cardiac Sympathetic Denervation on the Ventricular Fibrillation Threshold," The American Journal of Cardiology, vol. 37, pp. 1034-1040 (Jun. 1976).
Schwartz, et al., "Long term vagal stimulation in patients with advanced heart failure. First experience in man," European Journal of Heart Failure, 10, pp. 884-891 (2008).
Schwartz, et al., "Sympathetic-parasympathetic interaction in health and disease: abnormalities and relevance in heart failure," Heart Fail Rev, 16, pp. 101-107 (2011).
Seta, et al., "Basic Mechanisms in Heart Failure: The Cytokine Hypotehsis," Journal of Cardiac Failure, vol. 2, No. 3, pp. 243-249 (1996).
Sha, et al., "Low-Level Right Vagal Stimulation: Anticholinergic and Antiadrenergic Effects," J Cardiovasc Electrophysiol, pp. 1-7 (Feb. 2011).
Shamoon, et al., The Diabetes Control and Complications Trial Research Group, "The effect of intensive treatment of diabetes on the development and progression of long-term complications in insulin-dependent diabetes mellitus," The New England Journal of Medicine, vol. 329, No. 14, pp. 977-986 (Sep. 30, 1993).
Shannon, "A Model of Safe Levels for Electrical Stimulation," IEEE Transactions on Biomedical Engineering, vol. 39, No. 4, pp. 424-426 (Apr. 1992).
Shen, et al., "Continuous Low-Level Vagus Nerve Stimulation Reduces Stellate Ganglion Nerve Activity and Paroxysmal Atrial Tachyarrhythmias in Ambulatory Canines," Circulation, Journal of the American Heart Association, 123, pp. 2204-2212 (2011).
Shen, et al., "Low-level vagus nerve stimulation upregulates small conductance calcium-activated potassium channels in the stellate ganglion," Heart Rhythm, vol. 10, No. 6, pp. 910-915 (2013).
Shinohara, et al., "Heart Failure Decreases Nerve Activity in the Right Atrial Ganglionated Plexus," J Cardiovasc Electrophysiol, pp. 1-9 (2011).
Shioi, et al., "Increased Expression of Interleukin-1B and Monocyte Chemotactic and Activating Factor/Monocyte Chemoattractant Protein-1 in the Hypertrophied and Failing Heart with Pressure Overload," Circ Res., 81, pp. 664-671 (1997).
Singal, et al., "The role of oxidative stress in the genesis of heart disease," Cardiovascular Research, 40, pp. 426-432 (1998).
Spuck, et al., "Right-sided vagus nerve stimulation in humans: An effective therapy?" Epilepsy Research, pp. 1-3 (2008).
Stein, et al., "A Simple Method to Identify Sleep Apnea Using Holter Recordings," J Cardiovasc Electrophysiol, vol. 14, pp. 467-473 (May 2003).
Stein, et al., "Feasibility of Using Mobile Cardiac Outpatient Telemetry (MCOT) to Identify Severe Sleep Disorders" (2009).
Stieber, et al., "Bradycardic and proarrhythmic properties of sinus node inhibitors," Abstract, Molecular Pharmacology, 69(4):1328-37 (2006).
Taylor, et al., "The unequal influences of the left and right vagi on the control of the heart and pulmonary artery in the rattlesnake, *Crotalus durissus*," The Journal of Experimental Biology, 212, pp. 145-151 (2009).
Thayer, et al., "The role of vagal function in the risk for cardiovascular disease and mortality," Biological Psychology, 74, pp. 224-242 (2007).
Thollon, et al., "Electrophysiological effects of S 16257, a novel sino-atrial node modulator, on rabbit and guinea-pig cardiac preparations: comparison with UL-FS 49," Abstract, British Journal of Pharmacology, 112(1):37-42 (1994).
Tosato, et al., "Quasi-trapezoidal pulses to selectively block the activation of intrinsic laryngeal muscles during vagal nerve stimulation," J. Neural Eng., 4, pp. 205-212 (2007).
Tsutsumi, et al., "Modulation of the myocardial redox state by vagal nerve stimulation after experimental myocardial infarction," Cardiovascular Research, 77, pp. 713-721 (2008).
Tyler, et al., "Chapter 17—Electrodes for the Neural Interface," Neuromodulation, Academic Press (2009).
Ulphani, et al., "Quantitative analysis of parasympathetic innervation of the porcine heart," Heart Rhythm, 7, pp. 1113-1119 (2010).
Uthman, et al., "Effectiveness of vagus nerve stimulation in epilepsy patients. A 12-year observation," Neurology, 63, pp. 1124-1126 (2004).
Van Stee, "Autonomic Innervation of the Heart," Environmental Health Perspectives, vol. 26, pp. 151-158 (1978).
Vanoli, et al., "Vagal stimulation and prevention of sudden death in conscious dogs with a healed myocardial infarction," Circulation Research, Journal of the American Heart Association, 68, pp. 1471-1481 (1991).
Vasan,. et al., "Inflammatory Markers and Risk of Heart Failure in Elderly Subjects Without Prior Myocardial Infarction," Circulation, Journal of the American Heart Association, 107, pp. 1486-1491 (2003).
Vassalle, et al., "An Analysis of Arrhythmias Induced by Ouabain in Intact Dogs," Circulation Research, Journal of the American Heart Association, 13, pp. 132-148 (1963).
Velagaleti, et al., "Long-Term Trends in the Incidence of heart Failure After Myocardial Infarction," 118, pp. 2057-2062 (2008).
Verrier, et al., "Microvolt T-Wave Alternans," Journal of the American College of Cardiology, vol. 58, No. 13, pp. 1309-1324 (2011).
Vimercati, et al., "Acute vagal stimulation attenuates cardiac metabolic response to B-adrenergic stress," the Journal of Physiology,vol. 500, No. 23, pp. 6065-6074 (2012).
Wang, et al., "Nicotinic acetylcholine receptor alpha-7 subunit is an essential regulator of inflammation," Nature, vol. 421, pp. 384-388 (Jan. 23, 2003).
Wang, et al., "Synaptic and Neurotransmitter Activation of Cardiac Vagal Neurons in the Nucleus Ambiguus," Annals New York Academy of Sciences, pp. 237-246 (2001).
Waninger, et al., "Characterization of Atrioventricular Nodal Response to Electrical Left Vagal Stimulation," Annals of Biomedical Engineering, vol. 27, pp. 758-762 (1999).
Wann, "Behavioural signs of depression and apoptosis in the limbic system following myocardial infarction: effects of sertraline," Journal of Psychopharmacology, 23(4), pp. 451-459 (2009).
Wann, et al., "Vulnerability for apoptosis in the limbic system after myocardial infarction in rats: a possible model for human postinfarct major depression," J Psychiatry Neurosci, 32(1):11-6, pp. 11-16 (2007).
Watkins, et al., "Cytokine-to-Brain Communication: A Review & Analysis of Alternative Mechanisms," Life Sciences, vol. 57, No. 11, pp. 1011-1026 (1995).

(56) References Cited

OTHER PUBLICATIONS

Whyte, et al., "Reactive oxygen species modulate neuronal excitability in rat intrinsic cardiac ganglia," Auton Neurosci, 150(1-2), pp. 45-52 (Oct. 5, 2009).
Yang, et al., "Sustained increases in heart rate induced by time repetition of vagal stimulation in dogs," Am. J. Physiol., 249, pp. H703-H709 (1985).
Yin, et al., "Independent prognostic value of elevated high-sensitivity C-reactive protein in chronic heart failure," American Heart Journal, vol. 147, No. 5, pp. 931-938 (2004).
Yndestad, et al., "Systemic inflammation in heart failure—The whys and wherefores," Heart Fail Rev, 11, pp. 83-92 (2006).
Yoo, et al., "High-resolution measurement of electrically-evoked vagus nerve activity in the anesthetized dog," J. Neural Eng., 10, pp. 1-9 (2013).
Yoo, et al., "Selective Control of Physiological Responses by Temporally-Patterned Electrical Stimulation of the Canine Vagus Nerve," 33rd Annual International Conference of the IEEE EMBS (2011).
Yu, et al., "Interactions between atrial electrical remodeling and autonomic remodeling: How to break the vicious cycle," Heart Rhythm, 9, pp. 804-809 (2012).
Yu, et al., "Low-level transcutaneous electrical stimulation of the auricular branch of the vagus nerve: A noninvasive approach to treat the initial phase of atrial fibrillation," Heart Rhythm, 10, pp. 428-435 (2013).
Yuan, et al., "Gross and Microscopic Anatomy of the Canine Intrinsic Cardiac Nervous System," The Anatomical Record, 239, pp. 75-87 (1994).
Yusuf, et al., "Changes in Hypertension Treatment and in Congestive Heart Failure Mortality in the United States," Hypertension, Journal of the American Heart Association, 13:I74-I179 (1989).
Zhang, et al., "Arrhythimias and vagus nerve stimulation," Heart Fail Rev, 16, pp. 147-161 (2011).
Zhang, et al., "Chronic Vagus Nerve Stimulation Improves Autonomic Control and Attenuates Systemic Inflammation and Heart Failure Progression in a Canine High-Rate Pacing Model," Journal of the American Heart Association, Circ Heart Fail, 2, pp. 692-699 (2009).
Zhang, et al., "Involvement of activated astrocyte and microglia of locus coeruleus in cardiac pain processing after acute cardiac injury," Neurol Res, 31, pp. 432-438 (2009).
Zhang, et al., "Relationship between right cervical vagus nerve stimulation and atrial fibrillation inducibility: Therapeutic intensities do not increase arrhythmogenesis," Heart Rhythm, 6, pp. 244-250 (2009).
Zhang, et al., "Therapeutic Effects of Selective Atrioventricular Node Vagal Stimulation in Atrial Fibrillation and Heart Failure," Journal of Cardiovascular Electrophysiology, vol. 24, Issue 1, pp. 86-91 (2012).
Zheng, et al., "Vagal stimulation markedly suppresses arrhythmias in conscious rats with chronic heart failure after myocardial infarction," Proceedings of the 2005 IEEE (2005).
Zipes, et al., "Effects of selective vagal and stellate ganglion stimulation on atrial refractoriness," Cardiovascular Research, 8, pp. 647-655 (1974).
Zucker, et al., "Chronic Baroreceptor Activation Enhances Survival in Dogs with Pacing-Induced Heart Failure," Journal of the American Heart Association, Hypertension (2007).
PCT Application No. PCT/US2015/020116, Search Report and Written Opinion dated Jul. 6, 2015, 12 pages.

\* cited by examiner

40

50

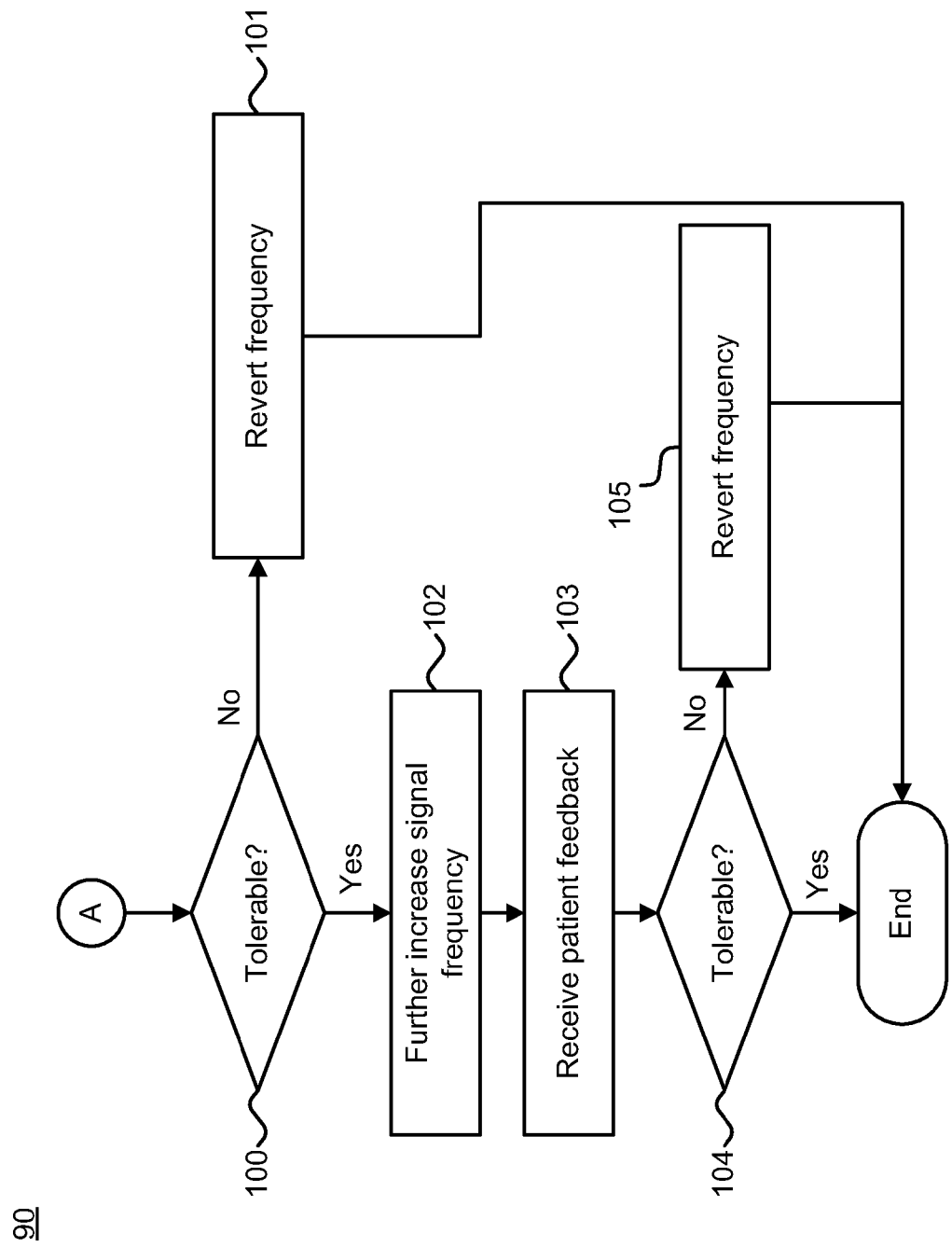

IMPLANTABLE NEUROSTIMULATOR FOR PROVIDING ELECTRICAL STIMULATION OF CERVICAL VAGUS NERVES FOR TREATMENT OF CHRONIC CARDIAC DYSFUNCTION WITH BOUNDED TITRATION

CROSS-REFERENCE TO RELATED APPLICATIONS

This patent application is a continuation of U.S. patent application Ser. No. 14/179,813, filed Feb. 13, 2014, now U.S. Pat. No. 8,965,522 issued Apr. 15, 2014, which is a divisional of U.S. patent application Ser. No. 13/931,961, filed Jun. 30, 2013, now U.S. Pat. No. 8,700,150 issued Apr. 15, 2014, which is a continuation-in-part of U.S. patent application Ser. No. 13/352,244, filed Jan. 17, 2012, now U.S. Pat. No. 8,571,654 issued Oct. 29, 2013, the disclosures of which are incorporated by reference in their entireties.

FIELD

This application relates in general to chronic cardiac dysfunction therapy and, in particular, to an implantable neurostimulator for providing electrical stimulation of cervical vagus nerves for treatment of chronic cardiac dysfunction with bounded titration.

BACKGROUND

Vagal nerve stimulation (VNS), therapeutic electrical stimulation of a patient's cervical vagus nerve, is used for treatment of multiple health conditions, including clinical treatment of drug-refractory epilepsy and depression. VNS has also been proposed for therapeutic treatment of heart conditions such as Congestive Heart Failure (CHF), a chronic medical condition in which the heart is unable to pump sufficient blood to meet the body's needs. For instance, VNS has been demonstrated in canine studies as efficacious in simulated treatment of atrial fibrillation (AF) and heart failure, such as described in Zhang et al., "Therapeutic Effects of Selective Atrioventricular Node Vagal Stimulation in Atrial Fibrillation and Heart Failure," J. Cardiovasc. Electrophysiol., Vol. 24, pp. 86-91 (January 2013), the disclosure of which is incorporated by reference.

VNS therapy commonly requires an implantation of a neurostimulator, a surgery requiring several weeks of recovery before a patient can start receiving VNS therapy. Even after the recovery, the neurostimulator does not immediately start delivering a full therapeutic dose of VNS to avoid causing significant patient discomfort and other undesirable side effects. Instead, to allow the patient to adjust to the VNS therapy, the intensity is gradually up titrated over a period of time under a control of a physician. Medically, such a titration can be completed in a period not exceeding two months. The titration can take significantly longer in practice because the increase in intensity must generally be performed by a physician or another healthcare professional. Thus, for every step in the titration to take place, the patient has to visit the physician's office. These visits generally occur once every one to three months due to scheduling conflicts, and can extend the titration process to as much as a year, during which the patient in need of VNS does not receive the VNS at the full therapeutic intensity.

The medically unnecessary delays in delivering therapeutic levels of VNS can further accumulate if the therapy is disrupted following the initial titration, such as if the implanted VNS neurostimulator runs out of power. Power for a conventional VNS neurostimulator is typically provided by an onboard battery. Delivering therapeutic VNS through an implantable neurostimulator presents battery longevity concerns similar to other types of implantable pulse generators, although a VNS neurostimulator is therapeutic and non-life sustaining Still, as the duty cycle of a VNS neurostimulator can at times be near constant, battery depletion can occur at a faster rate than with cardiac pacemakers, implantable cardioverter defibrillators (ICDs) and similar implantable devices that are triggered relatively infrequently under normal conditions. The in-service lifetime of a conventional VNS neurostimulator typically varies from three to seven years, depending upon programming, particularly duty cycle and stimulation intensity. As well, an increase in lead impedance can further cause premature battery depletion. Battery depletion necessitates eventual neurostimulator explantation and replacement, with attendant surgical risks of injury and infection. The disruption in therapy caused by the surgery requires a new cycle of titration of therapeutic intensity, which as described above, can take up to a year. Thus, a patient using a conventional VNS stimulator can be subjected to repeated, prolonged, and medically unjustified delays in receiving VNS stimulation that can be harmful to the patient's health.

In addition to the challenges associated with conventional VNS stimulators described above, conventional VNS stimulators do not achieve optimum effectiveness in treating the underlying causes of CHF. CHF, as well as other forms of chronic cardiac dysfunction, are generally attributed to an autonomic imbalance of the sympathetic and parasympathetic nervous systems that, if left untreated, can lead to cardiac arrhythmogenesis, progressively worsening cardiac function and eventual patient death. Furthermore, CHF is pathologically characterized by an elevated neuroexitatory state and is accompanied by physiological indications of impaired arterial and cardiopulmonary baroreflex function with reduced vagal activity.

Experimental VNS for cardiac therapy has focused on the efferent nerves of the parasympathetic nervous system, such as described in Sabbah et al., "Vagus Nerve Stimulation in Experimental Heart Failure," Heart Fail. Rev., 16:171-178 (2011), the disclosure of which is incorporated by reference. Sabbah discusses canine studies using a VNS system manufactured by BioControl Medical Ltd., Yehud, Israel, that includes an electrical pulse generator, right ventricular endocardial sensing lead, and right vagus nerve cuff stimulation lead. The sensing lead enables closed loop synchronization to the cardiac cycle; stimulation is delivered only when heart rate increases above a preset threshold. An asymmetric tri-polar nerve cuff electrode provides cathodic induction of action potentials while simultaneously applying asymmetric anodal blocks that lead to preferential activation of vagal efferent fibers. Stimulation is provided at an intensity and frequency intended to measurably reduce basal heart rate by ten percent by preferential stimulation of efferent vagus nerve fibers leading to the heart while blocking afferent neural impulses to the brain. The degree of therapeutic effect on parasympathetic activation occurs through incidental recruitment of afferent parasympathetic nerve fibers in the vagus, as well as through recruitment of efferent fibers.

Other uses of electrical nerve stimulation for therapeutic treatment of cardiac and physiological conditions are described. For instance, U.S. Pat. No. 8,219,188, issued Jul. 10, 2012 to Craig discloses synchronization of vagus nerve stimulation with a physiological cycle, such as the cardiac or respiratory cycle, of a patient. Electrical stimulation is applied to the vagus nerve at a selected point in the physiological cycle correlated with increased afferent conduction, such as a point from about 10 msec to about 800 msec after an R-wave of the patient's ECG, optionally during inspiration by the patient; to increase heart rate variability, such as a point from about 10 msec to about 800 msec after an R-wave of the patient's ECG, optionally during expiration by the patient; not correlated with increased efferent conduction on the vagus nerve; to generate efferent electrical activity on the vagus nerve; or upon the detection of a symptom of a medical condition. In a further embodiment, conventional VNS is applied to the vagus nerve along with microburst electrical signals, which is a portion of a therapeutic electrical signal having a limited plurality of pulses, separated from one another by interpulse intervals, and a limited burst duration, separated from one another by interburst periods. Stimulation may be applied to generate efferent electrical activity on the nerve in a direction away from the central nervous system; through a "blocking" type of electrical signal, such that both afferent and efferent electrical activity on the nerve is prevented from traveling further; or wherein afferent fibers are stimulated while efferent fibers are not stimulated or are blocked, and vice versa. By applying a series of microbursts to the vagus nerve, enhanced vagal evoked potentials (eVEP) are produced in therapeutically significant areas of the brain, in contrast to conventional VNS alone, which fails to produce eVEP.

U.S. Pat. No. 6,600,954, issued Jul. 29, 2003 to Cohen et al. discloses a method and apparatus for selective control of nerve fiber activations for reducing pain sensations in the legs and arms. An electrode device is applied to a nerve bundle capable of generating, upon activation, unidirectional action potentials that propagate through both small diameter and large diameter sensory fibers in the nerve bundle, and away from the central nervous system.

U.S. Pat. No. 6,684,105, issued Jan. 27, 2004 to Cohen et al. discloses an apparatus for treatment of disorders by unidirectional nerve stimulation. An apparatus for treating a specific condition includes a set of one or more electrode devices that are applied to selected sites of the central or peripheral nervous system of the patient. For some applications, a signal is applied to a nerve, such as the vagus nerve, to stimulate efferent fibers and treat motility disorders, or to a portion of the vagus nerve innervating the stomach to produce a sensation of satiety or hunger. For other applications, a signal is applied to the vagus nerve to modulate electrical activity in the brain and rouse a comatose patient, or to treat epilepsy and involuntary movement disorders.

U.S. Pat. No. 7,123,961, issued Oct. 17, 2006 to Kroll et al. discloses stimulation of autonomic nerves. An autonomic nerve is stimulated to affect cardiac function using a stimulation device in electrical communication with the heart by way of three leads suitable for delivering multi-chamber stimulation and shock therapy. For arrhythmia detection, the device utilizes atrial and ventricular sensing circuits to sense cardiac signals to determine whether a rhythm is physiologic or pathologic. The timing intervals between sensed events are classified by comparing them to a predefined rate zone limit and other characteristics to determine the type of remedial therapy needed, which includes bradycardia pacing, anti-tachycardia pacing, cardioversion shocks (synchronized with an R-wave), or defibrillation shocks (delivered asynchronously).

U.S. Pat. No. 7,225,017, issued May 29, 2007 to Shelchuk discloses terminating ventricular tachycardia in connection with any stimulation device that is configured or configurable to stimulate nerves, or stimulate and shock a patient's heart. Parasympathetic stimulation is used to augment anti-tachycardia pacing, cardioversion, or defibrillation therapy. To sense atrial or ventricular cardiac signals and provide chamber pacing therapy, particularly on the left side of the heart, the stimulation device is coupled to a lead designed for placement in the coronary sinus or its tributary veins. Cardioversion stimulation is delivered to a parasympathetic pathway upon detecting a ventricular tachycardia. A stimulation pulse is delivered via the lead to electrodes positioned proximate to the parasympathetic pathway according to stimulation pulse parameters based at least in part on the probability of reinitiation of an arrhythmia.

U.S. Pat. No. 7,277,761, issued Oct. 2, 2007 to Shelchuk discloses vagal stimulation for improving cardiac function in heart failure patients. An autonomic nerve is stimulated to affect cardiac function by way of three leads suitable for delivering multi-chamber endocardial stimulation and shock therapy. When the stimulation device is intended to operate as an implantable cardioverter-defibrillator (ICD), the device detects the occurrence of an arrhythmia, and applies a therapy to the heart aimed at terminating the detected arrhythmia. Defibrillation shocks are generally of moderate to high energy level, delivered asynchronously, and pertaining exclusively to the treatment of fibrillation.

U.S. Pat. No. 7,295,881, issued Nov. 13, 2007 to Cohen et al. discloses nerve branch-specific action potential activation, inhibition and monitoring. Two preferably unidirectional electrode configurations flank a nerve junction from which a preselected nerve branch issues with respect to the brain. Selective nerve branch stimulation can be used in conjunction with nerve-branch specific stimulation to achieve selective stimulation of a specific range of fiber diameters, substantially restricted to a preselected nerve branch, including heart rate control, where activating only the vagal B nerve fibers in the heart, and not vagal A nerve fibers that innervate other muscles, can be desirous.

U.S. Pat. No. 7,778,703, issued Aug. 17, 2010 to Gross et al. discloses selective nerve fiber stimulation for treating heart conditions. An electrode device is coupled to a vagus nerve and a control unit applies stimulating and inhibiting currents to the vagus nerve, which are capable of respectively inducing action potentials in a therapeutic direction in first and second sets of nerve fibers in the vagus nerve and inhibiting action potentials in the therapeutic direction in the second set of nerve fibers only. The nerve fibers in the second set have larger diameters than the first set's nerve fibers. Typically, the system is configured to treat heart failure or heart arrhythmia, such as AF or tachycardia by slowing or stabilizing the heart rate, or reducing cardiac contractility.

U.S. Pat. No. 7,813,805, issued Oct. 12, 2010 to Farazi and U.S. Pat. No. 7,869,869, issued Jan. 11, 2011 to Farazi both disclose subcardiac threshold vagus nerve stimulation. A vagus nerve stimulator is configured to generate electrical pulses below a cardiac threshold, which are transmitted to a vagus nerve, so as to inhibit or reduce injury resulting from ischemia. For arrhythmia detection, a heart stimulator utilizes atrial and ventricular sensing circuits to sense cardiac signals to determine whether a rhythm is physiologic or pathologic. In low-energy cardioversion, an ICD device typically delivers a cardioversion stimulus synchronously with a QRS complex. If anti-tachycardia pacing or cardioversion fails to terminate a tachycardia, after a programmed time interval or if the tachycardia accelerates, the ICD device initiates defibrillation.

U.S. Patent App. Pub. No. 2010/0331908, filed Sep. 10, 2010 by Farazi discloses subcardiac threshold vagus nerve stimulation in which a vagal nerve stimulator generates electrical pulses below a cardiac threshold of the heart for treating an ischemia of the heart, or for reducing a defibrillation threshold of the heart. The cardiac threshold is a threshold for energy delivered to the heart above which there is a slowing of the heart rate or the conduction velocity. In operation, the vagal nerve stimulator generates the electrical pulses below the cardiac threshold, that is, subcardiac threshold electrical pulses, such that the beat rate of the heart is not affected. Although the function of the vagal nerve stimulator is to treat an ischemia, or to reduce a defibrillation threshold of the heart, in other embodiments, the vagal nerve stimulator may function to treat heart failure, reduce an inflammatory response during a medical procedure, stimulate the release of insulin for treating diabetes, suppress insulin resistance for treating diabetes, or treat an infarction of the heart.

U.S. Pat. No. 7,634,317, issued Dec. 15, 2009, to Ben-David et al. discloses techniques for applying, calibrating and controlling nerve fiber stimulation, which includes a vagal stimulation system comprising a multipolar electrode device that is applied to a portion of a vagus nerve (a left vagus nerve and/or right vagus nerve), which innervates a heart of a subject. Alternatively, the electrode device is applied to an epicardial fat pad, a pulmonary vein, a carotid artery, a carotid sinus, a coronary sinus, a vena cava vein, a right ventricle, or a jugular vein. The system is utilized for treating a heart condition such as heart failure and/or cardiac arrhythmia; the vagal stimulation system further comprises an implantable or external control unit, which typically communicates with electrode device over a set of leads. Typically, the control unit drives the electrode device to (i) apply signals to induce the propagation of efferent nerve impulses towards heart, and (ii) suppress artificially-induced afferent nerve impulses towards a brain of the subject, to minimize unintended side effects of the signal application; the efferent nerve pulses in vagus nerve are typically induced by the electrode device to regulate the heart rate of the subject.

Finally, U.S. Pat. No. 7,885,709, issued Feb. 8, 2011 to Ben-David discloses nerve stimulation for treating disorders. An electrode device stimulates the vagus nerve, so as to modify heart rate variability, or to reduce heart rate, by suppressing the adrenergic (sympathetic) system. Typically, the system is configured to treat heart failure or heart arrhythmia. Therapeutic effects of reduction in heart rate variability include the narrowing of the heart rate range, thereby eliminating very slow heart rates and very fast heart rates. For this therapeutic application, the control unit is typically configured to reduce low-frequency heart rate variability, and to adjust the level of stimulation applied based on the circadian and activity cycles of the subject. Therapeutic effects also include maximizing the mechanical efficiency of the heart by maintaining relatively constant ventricular filling times and pressures.

Notwithstanding, a need remains for an approach to therapeutically treating chronic cardiac dysfunction through a neurostimulator that allows to avoid medically unjustified delays in VNS therapy associated with titration of intensity of VNS stimulation.

SUMMARY

Excessive sustained activation of the sympathetic nervous system has a deleterious effect on long term cardiac performance and on the quality of life and survival of patients suffering from chronic cardiac dysfunction. CHF patients are at increased risk of atrial tachyarrhythmias, such as AF and atrial flutter, and ventricular tachyarrhythmias, such as ventricular tachycardia (VT) and ventricular fibrillation (VF)), particularly when the underlying morbidity is a form of coronary artery disease, cardiomyopathy, mitral valve prolapse, or other valvular heart disease. Low intensity peripheral neurostimulation therapies that target the imbalance of the autonomic nervous system have been shown to improve clinical outcomes. Thus, bi-directional autonomic regulation therapy is delivered to the cervical vagus nerve at an intensity that is insufficient to elicit pathological or acute physiological side effects and without the requirement of an enabling physiological feature or triggering physiological marker. Letting a patient in need of such therapy to control the therapy titration following the implantation of a VNS neurostimulator allows the patient to receive VNS stimulation at a full therapeutic intensity sooner than if the titration is performed entirely under a control of a healthcare professional. Furthermore, placing physician-defined boundaries on the titration mitigates the risks associated with over-aggressive patient titration of the stimulation.

One embodiment provides a system for providing electrical stimulation of cervical vagus nerves for treatment of chronic cardiac dysfunction with bounded titration. The system includes a patient-operable external controller configured to transmit a plurality of unique signals including a unique signal associated with an up-titration command. The system further includes an implantable neurostimulator. The implantable neurostimulator includes a pulse generator configured to deliver electrical therapeutic stimulation tuned to restore autonomic balance through continuously-cycling, intermittent and periodic electrical pulses simultaneously delivered at an intensity that avoids acute physiological side effects and with an unchanging cycle not triggered by physiological markers in a manner that results in creation and propagation (in both afferent and efferent directions) of action potentials within neuronal fibers comprising a cervical vagus nerve of a patient through a pair of helical electrodes via an electrically coupled nerve stimulation therapy lead. The implantable neurostimulator also includes a recordable memory storing an autotitration operating mode that includes a maximum stimulation intensity and is configured to increase an intensity of the delivered electrical therapeutic stimulation up to a level not exceeding the maximum stimulation intensity upon receipt of the unique signal associated with the up-titration command.

A further embodiment provides an implantable neurostimulator-implemented method for providing electrical stimulation of cervical vagus nerves for treatment of chronic cardiac dysfunction with bounded titration. An implantable neurostimulator that includes a pulse generator configured to deliver electrical therapeutic stimulation in a manner that results in creation and propagation (simultaneously in both afferent and efferent directions) of action potentials within neuronal fibers comprising the cervical vagus nerve of a patient is provided. An autotitration operating mode is stored into a recordable memory, which includes: parametrically defining a maximum stimulation intensity of the electrical therapeutic stimulation deliverable under the autotitration operating mode; and parametrically defining a titration dose of the electrical therapeutic stimulation tuned to restore cardiac autonomous balance through continuously-cycling, intermittent and periodic electrical pulses at an intensity not exceeding the maximum stimulation intensity that avoids acute physiological side affects and with an unchanging cycle not triggered by physiological markers. The titration dose is therapeutically delivered to the vagus nerve independent of cardiac cycle via the pulse generator in the implantable neurostimulator through at least a pair of helical electrodes electrically coupled to the pulse generator via a nerve stimulation therapy lead. Upon receiving a remotely applied signal uniquely associated with an up-titration command from a patient-operable external controller, the titration dose intensity is increased to a level not exceeding the maximum stimulation intensity.

A still further embodiment provides a system for providing a bounded titration of electrical stimulation of cervical vagus nerves for treatment of chronic cardiac dysfunction following the stimulation start or disruption. The system includes a patient-operable external controller configured to transmit a unique signal associated with an up-titration command. The system further includes an implantable neurostimulator powered by a rechargeable battery in included in the neurostimulator. The neurostimulator includes a pulse generator configured to deliver electrical therapeutic stimulation tuned to restore autonomic balance through continuously-cycling, intermittent and periodic electrical pulses simultaneously delivered at an intensity that avoids acute physiological side effects and with an unchanging cycle not triggered by physiological markers in a manner that results in creation and propagation (in both afferent and efferent directions) of action potentials within neuronal fibers comprising a cervical vagus nerve of a patient through a pair of helical electrodes via an electrically coupled nerve stimulation therapy lead. The neurostimulator also includes a recordable memory storing an autotitration operating mode that includes a maximum stimulation intensity and that is configured to perform a stimulation autotitration following at least one of the neurostimulator's implantation into the patient and a disruption of the delivery of the electrical therapeutic stimulation caused by a depletion of the neurostimulator's power, the autotitration including an increase in intensity of the delivered electrical therapeutic stimulation, to a level not exceeding the maximum stimulation intensity, performed upon receipt of the unique signal associated with the up-titration command. The neurostimulator further includes an energy receiver configured to transcutaneously receive energy and recharge the rechargeable battery with the received energy.

By restoring autonomic balance, therapeutic VNS operates acutely to decrease heart rate, increase heart rate variability and coronary flow, reduce cardiac workload through vasodilation, and improve left ventricular relaxation. Over the long term, VNS provides the chronic benefits of decreased negative cytokine production, increased baroreflex sensitivity, increased respiratory gas exchange efficiency, favorable gene expression, renin-angiotensin-aldosterone system down-regulation, and anti-arrhythmic, anti-apoptotic, and ectopy-reducing anti-inflammatory effects. Furthermore, patient-controlled autotitration of VNS stimulation allows the patient to avoid the unnecessary delays associated with visiting a physician's office for every step in the titration to take place. Furthermore, providing the neurostimulator with a rechargeable battery allows to lessen the frequency of a disruption in therapy and the associated need to retitrate the therapy following a replacement of a neurostimulator with a depleted battery.

Still other embodiments of the present invention will become readily apparent to those skilled in the art from the following detailed description, wherein are described embodiments by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Changes in autonomic control of the cardiovascular systems of patients suffering from CHF and other cardiovascular diseases push the autonomic nervous system out of balance and favor increased sympathetic and decreased parasympathetic central outflow. The imbalance is accompanied by pronounced elevation of basal heart rate arising from chronic sympathetic hyperactivation along the neurocardiac axis. Medically unnecessary delays in providing CHF therapy to a patient can further deteriorate the patient's health.

Low intensity peripheral neurostimulation therapies that target the imbalance of the autonomic nervous system have been shown to improve clinical outcomes in patients treated for three to twelve months. Bi-directional autonomic regulation therapy results in simultaneous creation and propagation of efferent and afferent action potentials within the vagus nerve. In contrast to conventional approaches to VNS, the neurostimulation is delivered bi-directionally and at an intensity that is insufficient to elicit pathological or acute physiological side effects, such as acute cardiac arrhythmias, and without the requirement of an enabling physiological feature or triggering physiological marker, such as heart rate or heart rate variability (HRV), such as for purposes of timing stimulation delivery, to confirm therapeutic effect, or other ends. Here, upon continuously-cycling, intermittent and periodic low intensity stimulation of the cervical vagus nerve, action potentials propagate away from the stimulation site in two directions, efferently toward the heart to influence the intrinsic cardiac nervous system and the heart and afferently toward the brain to influence central elements of the nervous system.

Figure 1:
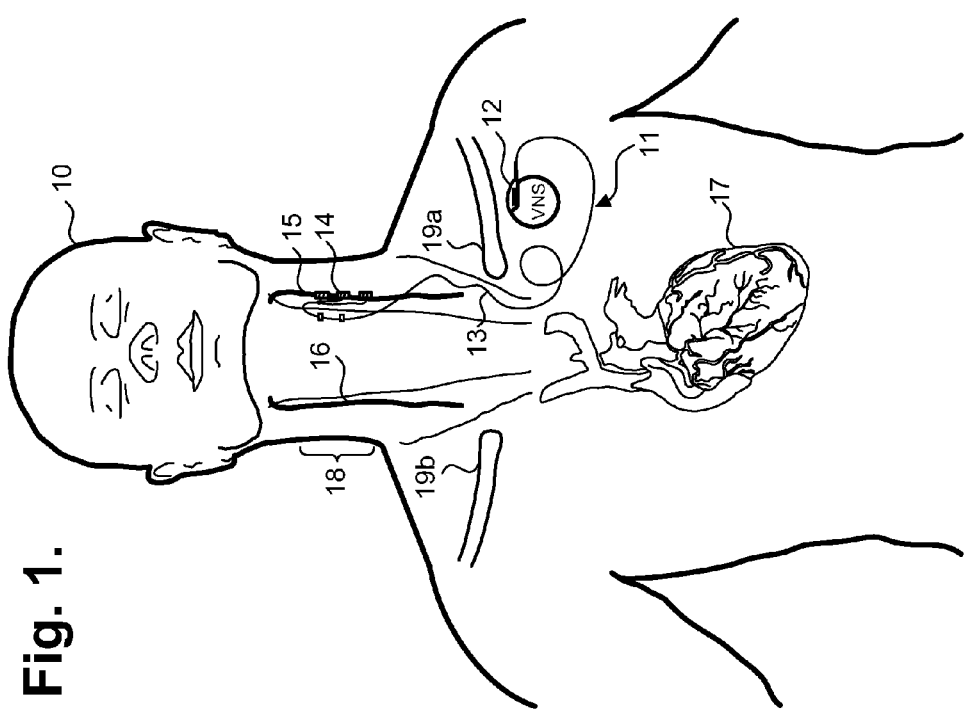
FIG. 1 is a front anatomical diagram showing, by way of example, placement of an implantable vagus stimulation device in a male patient, in accordance with one embodiment.

An implantable vagus nerve stimulator (neurostimulator), such as used to treat drug-refractory epilepsy and depression, can be adapted for use in managing chronic cardiac dysfunction through therapeutic bi-directional vagal stimulation. While the VNS therapy may not be delivered immediately at a full therapeutic intensity, allowing the patient to control the titration of intensity of VNS stimulation delivered to the patient makes this titration process ("autotitration") significantly faster when compared to a titration entirely controlled by a physician. In particular, the intensity of VNS delivered by the neurostimulator can be adjusted by a patient-operable external controller, which allows the patient to up-titrate the VNS within bounds set by in advance by a physician or another healthcare professional. Thus, by allowing the patient to perform up-titration of VNS intensity, the number of visits to a physician's office is reduced, which in turn reduces the length of the titration process. Furthermore, the neurostimulator can also be inductively charged in situ to counter battery depletion during operation, and preventing the need to perform an additional cycle of titration necessary when the neurostimulator is surgically replaced due to a depleted battery. FIG. 1 is a front anatomical diagram showing, by way of example, placement of an implantable vagus nerve stimulation (VNS) device 11 in a male patient 10, in accordance with one embodiment. The VNS provided through the stimulation device 11 operates under several mechanisms of action. These mechanisms include increasing parasympathetic outflow and inhibiting sympathetic effects by blocking norepinephrine release. More importantly, VNS triggers the release of acetylcholine (ACh) into the synaptic cleft, which has beneficial anti-arrhythmic, anti-apoptotic, and ectopy-reducing anti-inflammatory effects.

The implantable vagus stimulation device 11 includes at least three implanted components, an implantable neurostimulator 12, a therapy lead 13, and helical electrodes 14. The implantable vagus stimulation device 11 can be remotely accessed following implantation through an external programmer (not shown) and patient-operable external controller (not shown). For example, the implantable vagus stimulation device 11 can be remotely accessed following implantation through the external programmer by which the neurostimulator 12 can be remotely checked and programmed. In particular, the external programmer can be used to set parameters for delivering VNS stimulation, such as duty cycle, output current (amplitude), frequency, and pulse width, with these parameters defining the intensity at which VNS is delivered. For example, the external programmer can be used to program a set of maximum stimulation parameters of VNS therapy that the neurostimulator 12 can deliver under any operating mode. For a commercial device sold by Cyberonics, Inc., Houston, Tex., such parameters could be an output current of 3.5 MA, signal frequency of 30 Hz, and pulse width of 1000 μsec. Other parameters are possible.

Figure 7:
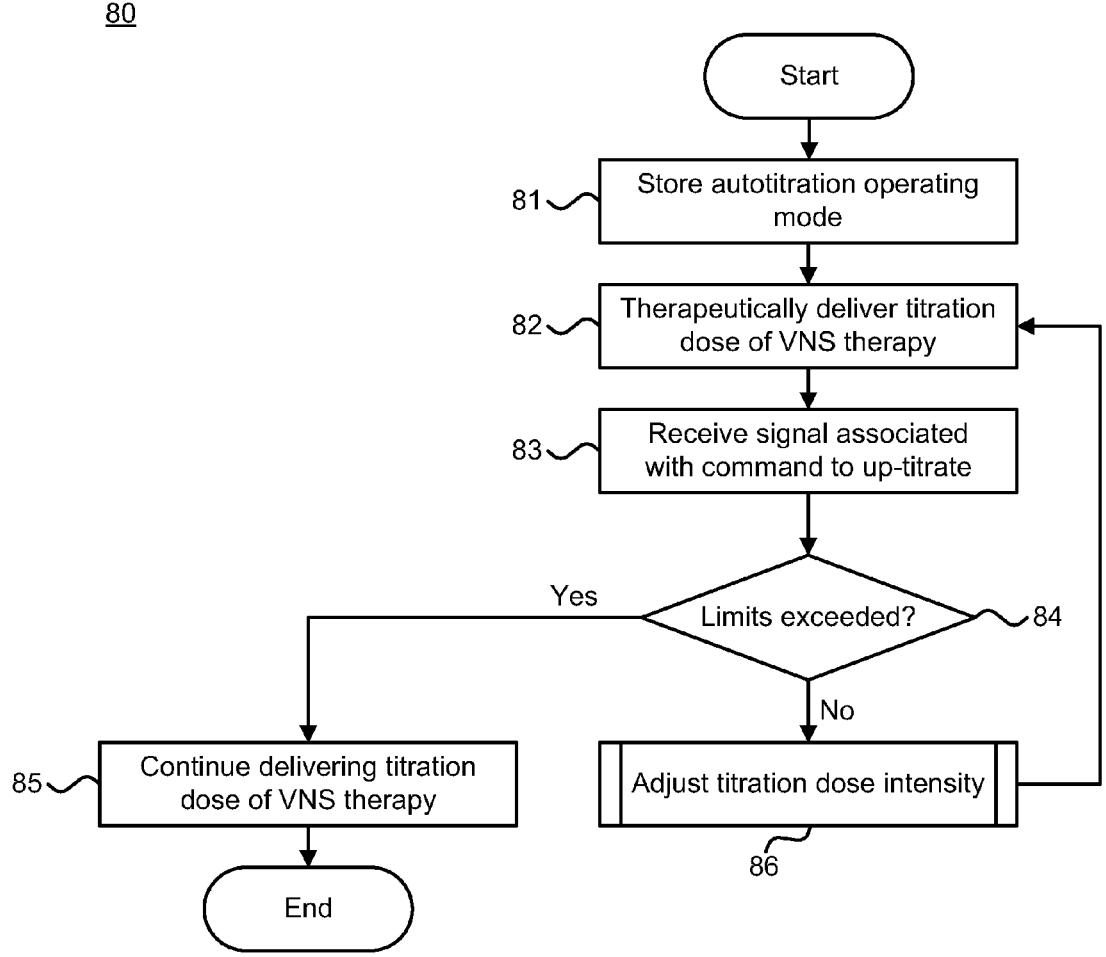
FIG. 7 is a flow diagram showing an implantable neurostimulator-implemented method for treatment of chronic cardiac dysfunction with bounded titration in accordance with one embodiment.
Figure 8:
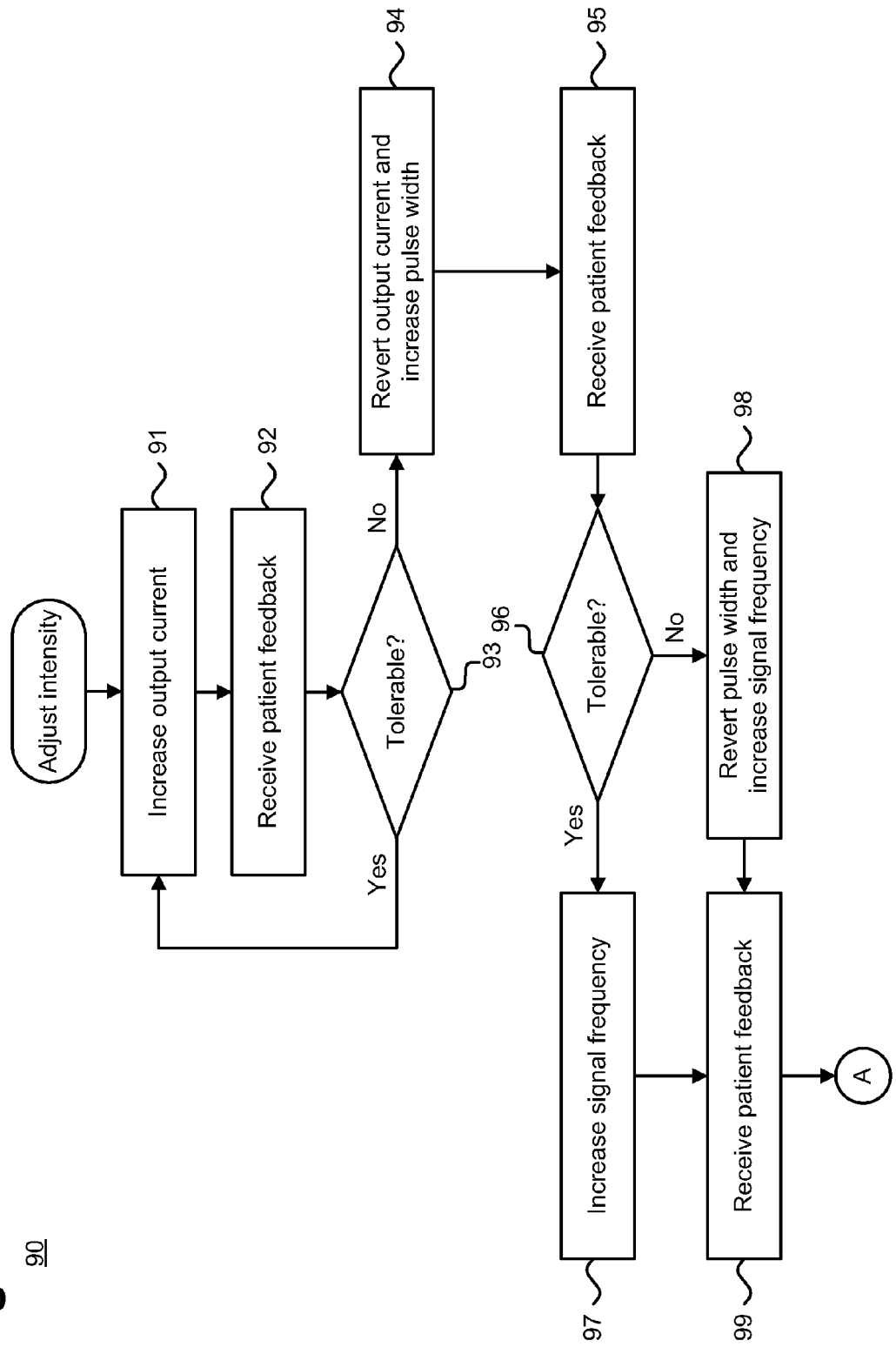
FIG. 8 is a flow diagram showing a routine for adjusting intensity of VNS therapy during autotitration based on patient feedback for the method of FIG. 7.

The external programmer can also be used by a healthcare professional to store into the neurostimulator 12 an autotitration operating mode, described in detail infra with reference to FIGS. 7 and 8, which directs delivery of VNS during the autotitration process under a control of a patient-operable external controller. The autotitration operating mode includes limits, or boundaries, of the patient-controlled autotitration. For example, the autotitration operating mode can include a set of one or more maximum stimulation parameters defining the maximum stimulation intensity of VNS therapy that the neurostimulator can deliver during the autotitration process; this limit prevents the patient 10 from autotitrating above the maximum stimulation intensity. Once the maximum stimulation intensity is achieved during the autotitration process, further up-titration is prevented, and the patient 10 needs to visit a healthcare professional's office, where the healthcare professional can use the external programmer to program into the neurostimulator 12 an updated set of maximum stimulation parameters. Other limitations can be included in the operating mode. For example, a patient 10 may be limited to performing autotitration according to a predefined schedule, with the permissible frequency of patient-controlled increases in intensity and the period of time during which the patient can perform the autotitration being programmed into the operating mode. Other limits are possible. As described further infra, with reference to FIGS. 7 and 8, the autotitration operating mode further defines the increments at which the stimulation parameters are increased during the autotitration as well as the adjustments of the stimulation parameters that occur if the patient 10 indicates that an increased level of stimulation is not tolerable. Other aspects of the autotitration process can be addressed by the operating mode.

A patient-operable external controller (not shown) allows the patient to control the autotitration process, subject to the limits set by the healthcare professional in the autotitration operating mode. The patient-operable external controller is configured to control the neurostimulator 12 by transmitting to the neurostimulator 12 unique signals associated with commands, such as a command to increase (up-titrate) intensity of VNS stimulation, or patient feedback regarding whether an increased intensity of VNS therapy is tolerable. The patient-operable external controller can also suspend indefinitely VNS stimulation by supplying a magnetic signal to the neurostimulator, as further described in detail in the commonly-assigned U.S. patent application, "Vagus Nerve Neurostimulator With Multiple Patient-Selectable Modes For Treating Chronic Cardiac Dysfunction," Ser. No. 13/352,244, filed on Jan. 17, 2012, now U.S. Pat. No. 8,571,654. Other functionality of the patient-operable external controller is possible, as described in U.S. Pat. No. 8,571,654 cited supra.

In one embodiment, the patient-operable external controller can be an external magnet, such as described in commonly-assigned U.S. Pat. No. 8,600,505, issued Dec. 3, 2013, entitled "Implantable Device For Facilitating Control Of Electrical Stimulation Of Cervical Vagus Nerves For Treatment Of Chronic Cardiac Dysfunction," the disclosure of which is incorporated by reference. In a further embodiment, the patient-operable external controller can be an external electromagnetic controller, such as described in U.S. Pat. No. 8,571,654 cited supra. Other types of patient-operable external controllers are possible. Together, the implantable vagus stimulation device 11, the external programmer, and one or more of the external controllers described above can form a VNS therapeutic delivery system.

The neurostimulator 12 is implanted in the patient's right or left pectoral region generally on the same side (ipsilateral) as the cervical vagus nerve 15, 16 to be stimulated, although other neurostimulator-vagus nerve configurations, including contra-lateral and bi-lateral, are possible. The helical electrodes 14 are generally implanted on the vagus nerve 15, 16 about halfway between the clavicle 19a-b and the mastoid process. The therapy lead 13 and helical electrodes 14 are implanted by first exposing the carotid sheath and chosen vagus nerve 15, 16 through a latero-cervical incision on the ipsilateral side of the patient's neck 18. The helical electrodes 14 are then placed onto the exposed nerve sheath and tethered. A subcutaneous tunnel is formed between the respective implantation sites of the neurostimulator 12 and helical electrodes 14, through which the therapy lead 13 is guided to the neurostimulator 12 and securely connected.

The stimulation device 11 bi-directionally stimulates the vagus nerve 15, 16 through multimodal application of continuously-cycling, intermittent and periodic electrical stimuli, which are parametrically defined through stored stimulation parameters and timing cycles according to various operating modes. While the autotitration operating mode described infra with reference to FIGS. 7 and 8 allows titration of VNS intensity under a control of a patient-operable external controller, other operating modes can be implemented by the stimulation device 11. For example, in further embodiments, tachycardia and bradycardia in VNS-titrated patients can be respectively managed, such as described in commonly-assigned U.S. patent application Ser. No. 13/673,766, filed on Nov. 9, 2012, entitled "Implantable Neurostimulator-Implemented Method for Managing Tachyarrhythmia Through Vagus Nerve Stimulation," published as U.S. Patent Application Publication No. 2014/0135862 A1, pending, and U.S. Pat. No. 8,688,212, issued Apr. 1, 2014, entitled "Implantable Neurostimulator-Implemented Method for Managing Bradycardia through Vagus Nerve Stimulation," the disclosures of which are incorporated by reference. In a still further embodiment, prolonged activation of the sympathetic nervous system during post-exercise recovery periods, particularly in patients with CCD, can be managed through application of a "boost" dose of VNS, such as described in commonly-assigned U.S. patent application Ser. No. 13/673,795, filed on Nov. 9, 2012, entitled "Implantable Neurostimulator-Implemented Method for Enhancing Post-Exercise Recovery through Vagus Nerve Stimulation," published as U.S. Patent Application Publication No. 2014/0135863 A1, pending, the disclosure of which is incorporated by reference.

Both sympathetic and parasympathetic nerve fibers are stimulated. Cervical vagus nerve stimulation results in the creation and propagation of action potentials (in both afferent and efferent directions) within neuronal fibers comprising the cervical vagus nerve from the site of stimulation to restore cardiac autonomic balance. Afferent action potentials propagate toward the parasympathetic nervous system's origin in the medulla in the nucleus ambiguus, nucleus tractus solitarius, and the dorsal motor nucleus, as well as towards the sympathetic nervous system's origin in the intermediolateral cell column of the spinal cord. Efferent action potentials propagate toward the heart 17 to activate the components of the heart's intrinsic nervous system. The helical electrodes 14 can be implanted on either the left or right vagus cervical nerve 15, 16. The right vagus nerve 16 has a moderately lower stimulation threshold than the left vagus nerve 15 for heart rate affects at the same parametric levels of VNS.

Figure 2A:
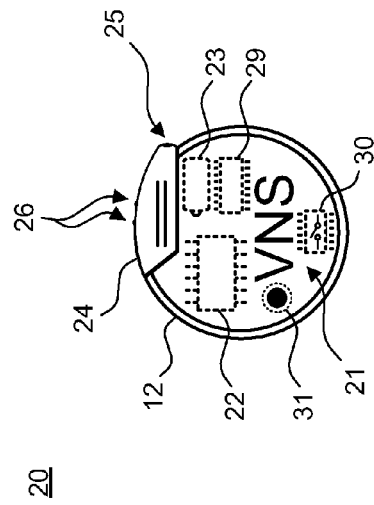
FIGS. 2A and 2B are diagrams respectively showing the rechargeable implantable neurostimulator for treatment of chronic cardiac dysfunction and the simulation therapy lead of FIG. 1.
Figure 2B:
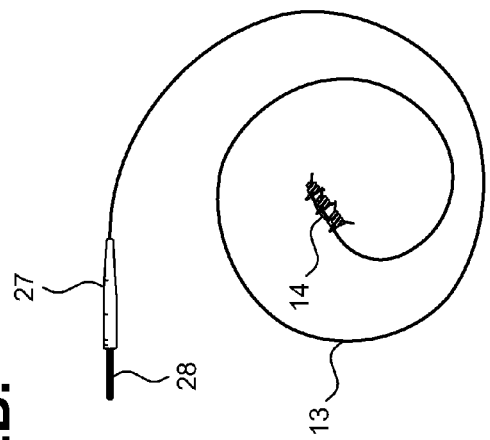

The VNS therapy is delivered autonomously to the patient's vagus nerve 15, 16 through three implanted components that include a neurostimulator 12, therapy lead 13, and helical electrodes 14. FIGS. 2A and 2B are diagrams respectively showing the implantable neurostimulator 12 and the stimulation therapy lead 13 of FIG. 1. In one embodiment, the neurostimulator 12 can be adapted from a VNS Therapy AspireSR Model 105 or Model 106 pulse generator, manufactured and sold by Cyberonics, Inc., Houston, Tex., although other manufactures and types of single-pin receptacle implantable VNS neurostimulators with or without integrated leadless heart rate sensors could also be used. The stimulation therapy lead 13 and helical electrodes 14 are generally fabricated as a combined assembly and can be adapted from a Model 302 lead, PerenniaDURA Model 303 lead, or PerenniaFLEX Model 304 lead, also manufactured and sold by Cyberonics, Inc., in two sizes based on helical electrode inner diameter, although other manufactures and types of single-pin receptacle-compatible therapy leads and electrodes could also be used.

Referring first to FIG. 2A, the neurostimulator 12 provides multimodal vagal stimulation. The neurostimulator 12 includes an electrical pulse generator that is tuned to restore autonomic balance by triggering action potentials that propagate bi-directionally (both afferently and efferently) within the vagus nerve 15, 16. The neurostimulator 12 includes an electrical pulse generator that is tuned to restore autonomic balance by triggering the creation of action potentials that propagate both afferently and efferently within the vagus nerve 15, 16. The neurostimulator 12 is enclosed in a hermetically sealed housing 21 constructed of a biocompatible, implantation-safe material, such as titanium. The housing 21 contains electronic circuitry 22 powered by a primary rechargeable battery 23, which can be a lithium-ion battery, such as lithium nickel manganese cobalt oxide. The electronic circuitry 22 is implemented using complementary metal oxide semiconductor (CMOS) integrated circuits that include a microprocessor controller that executes a control program according to stored stimulation parameters and timing cycles; a voltage regulator that regulates system power; logic and control circuitry, including a recordable memory 29 within the operating modes and stimulation parameters are stored, that controls overall pulse generator function, receives and implements programming commands from the external programmer, or other external source, collects and stores telemetry information, processes sensory input, and controls scheduled and sensory-based therapy outputs; a transceiver that remotely communicates with the external programmer using radio frequency signals; an antenna, which receives programming instructions and transmits the telemetry information to the external programmer; and a reed switch 30 that provides remote access to the operation of the neurostimulator 12 using the external programmer or the patient-operable external controller. The recordable memory 29 can include both volatile (dynamic) and persistent (static) forms of memory, such as firmware within which the stimulation parameters and timing cycles can be stored. Other electronic circuitry and components are possible.

Figure 3:
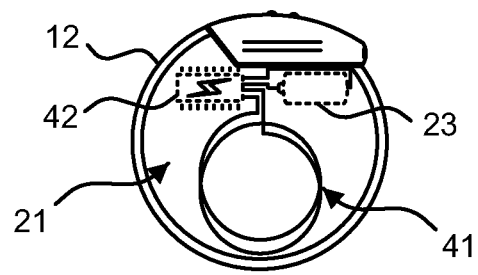
FIG. 3 is a diagram showing the charging components of the implantable neurostimulator of FIG. 1.

Power supplied to the neurostimulator 12 is provided by the rechargeable battery 23, which can be inductively charged by the patient 10 or caregiver as necessary to replenish the battery 23. Recharging the battery 23 allows delaying the disruption in delivery of VNS therapy caused by a depletion of the neurostimulator's 12 power, neurostimulator 12 explantation, and a subsequent need to perform another round of VNS titration. FIG. 3 is a diagram showing the charging components of the implantable neurostimulator 12 of FIG. 1. The rechargeable battery 23 is chargeable via inductive transcutaneous energy transfer. An electromagnetic coil 41 necessary to convert AC power into DC power, such as described in U.S. Pat. No. 5,350,413, issued Sep. 27, 1994 to Miller, the disclosure of which is incorporated by reference, is integrated into the housing 21 of the neurostimulator 12. In addition, charging circuitry 42 is coupled with the electromagnetic coil 41 and the rechargeable battery 23.

Figure 4:
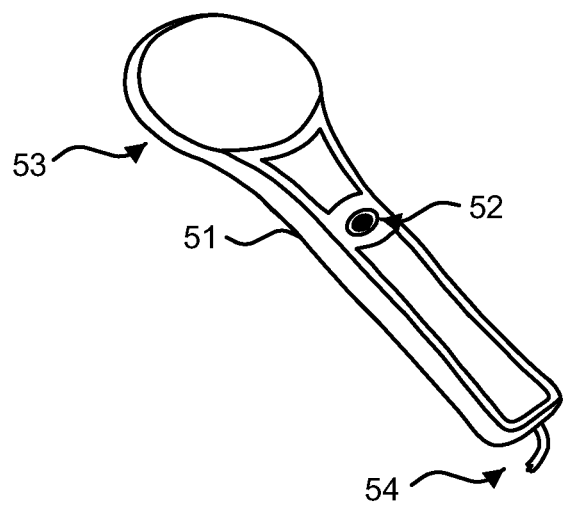
FIG. 4 is a diagram showing an external charger for use with the implantable neurostimulator of FIG. 1.

During charging, the patient 10 or other caregiver places an inductive charging wand over the implantation site of the neurostimulator 12. FIG. 4 is a diagram showing an external charger 50 for use with the implantable neurostimulator 12 of FIG. 1. The external charger 50 includes an inductive charging wand 51 that sends energy to the electromagnetic coil 14 through a transcutaneous inductive coupling, and the charging circuitry 42 converts the energy back into electrical current, which charges the onboard rechargeable battery 23. The inductive charging wand 51 encloses an inductive charging coil (not shown) on a distal end, which is placed over the implantation site of the neurostimulator 12. The inductive charging wand 51 is plugged into a wall outlet or other electrical power source with a power cord 54 or similar type of connector. Once placed over the implantation site, the patient 10 or caregiver presses a button 52 or other patient-operable control to start the charging of the neurostimulator 12.

The respective electromagnetic coils in the neurostimulator 12 and the inductive charging wand 51 form a transcutaneous inductive coupling when the button 52 is pressed, during which time alternating current energy is transferred into the neurostimulator 12, converted back into electrical current, and used to charge the rechargeable battery 23. Other ways for the neurostimulator 12 to transcutaneously receive energy from an external charging source are possible. For example, the neurostimulator 12 can include at least one photovoltaic cell, such as described in U.S. Patent Publication No. 2009/0326597, published Dec. 31, 2009, abandoned, the disclosure of which is incorporated by reference. In one embodiment, the photovoltaic cell is subcutaneously placed away from the housing 21 of the neurostimulator 12. The photovoltaic cell is electrically interfaced with the charging circuitry 42 via electrical wiring. The photovoltaic cell absorbs light passing through the patient's translucent layers of skin, and converts the light into electrical energy, which is then fed through the charging circuitry 42 into the rechargeable battery 23. The photovoltaic cell can absorb either the light naturally coming from the patient's surroundings, or light generated by an energy generator containing a light source, such as described in U.S. Pat. No. 6,961,619, issued Nov. 1, 2005, to Casey, the disclosure of which is incorporated by reference. In one embodiment, the energy generator is placed against the patient's skin in alignment with the location of the photovoltaic cell. Still other ways to transcutaneously transmit energy are possible.

Ordinarily, the charging circuitry 42 charges the rechargeable battery 23, but prevents overcharging beyond the limits of the battery. In a further embodiment, the charging circuitry 42 measures the rechargeable battery's state of charge for reporting status to the patient 10 or caregiver. The charging circuitry 42 is electrically interfaced with the microprocessor controller, and provides the state of charge of the rechargeable battery 23. The neurostimulator 12 can provide feedback concerning the state of charge by transmitting status information to the external programmer or another remotely-interfaceable interrogation device using a transceiver and the antenna, either at the request of the external programmer or when the state of charge reaches a predetermined level. The external programmer can be the programming wand, as described infra, or be included as part of the charging circuitry 42. In a further embodiment, the neurostimulator can transmit status information to the patient-operable external controller. Other ways of interacting with the charging circuitry 42 are possible.

Referring back to FIG. 2A, the neurostimulator 12 externally includes a header 24 to securely receive and connect to the therapy lead 13. In one embodiment, the header 24 encloses a receptacle 25 into which a single pin for the therapy lead 13 can be received, although two or more receptacles could also be provided, along with the requisite additional electronic circuitry 22. The header 24 internally includes a lead connector block (not shown) and a set of set screws 26.

In one embodiment, the housing 21 can also contain a heart rate sensor 31 that is electrically interfaced with the logic and control circuitry, which receives the patient's sensed heart rate or, alternatively, HRV, as sensory inputs. In a further embodiment, the heart rate sensor 31 is either external to or physically separate from the neurostimulator 12 proper, but is operatively coupled, either through physical wired connection or via wireless interface. The heart rate sensor 31 monitors heart rate or HRV using an ECG-type electrode. Through the electrode, the patient's heart beat can be sensed by detecting ventricular depolarization or similar physiology. In a further embodiment, a plurality of electrodes can be used to sense voltage differentials between electrode pairs, which can undergo signal processing for further cardiac physiological measures, for instance, detection of the P-wave, QRS complex, and T-wave. The heart rate sensor 31 provides the sensed heart rate or HRV to the control and logic circuitry as sensory inputs that can be used to determine the presence of arrhythmias, especially VT.

As mentioned above, the neurostimulator 12 can be interrogated preferably prior to implantation and throughout the therapeutic period with a healthcare provider-operable external programmer and programming wand (not shown) for checking proper operation, downloading recorded data, diagnosing problems, and programming operational parameters and operating modes, such as described in commonly-assigned U.S. Pat. No. 8,600,505, issued Dec. 3, 2013, and U.S. Pat. No. 8,571,654, cited supra. In particular, the neurostimulator 12 is interrogated prior to starting of titration of VNS therapy. In one embodiment, the external programmer executes application software specifically designed to interrogate the neurostimulator 12. The programming computer interfaces to the programming wand through a standardized wired or wireless data connection. The programming wand can be adapted from a Model 201 Programming Wand, manufactured and sold by Cyberonics, Inc. and the application software can be adapted from the Model 250 Programming Software suite, licensed by Cyberonics, Inc. Other configurations and combinations of external programmer, programming wand and application software are possible.

The neurostimulator 12 delivers VNS under control of the electronic circuitry 22. The stored stimulation parameters are programmable. Each stimulation parameter can be independently programmed to define the characteristics of the cycles of therapeutic stimulation and inhibition to ensure optimal stimulation for a patient 10. The programmable stimulation parameters include output current, signal frequency, pulse width, signal ON time, signal OFF time, magnet activation (for VNS specifically triggered by a magnetic signal, such as during the autotitration process in one embodiment), and reset parameters. Other programmable parameters are possible. In addition, sets or "profiles" of pre-selected stimulation parameters can be provided to physicians with the external programmer and fine-tuned to a patient's physiological requirements prior to being programmed into the neurostimulator 12, such as described in commonly-assigned U.S. Pat. No. 8,630,709, issued Jan. 14, 2014, entitled "Computer-Implemented System and Method for Selecting Therapy Profiles of Electrical Stimulation of Cervical Vagus Nerves for Treatment of Chronic Cardiac Dysfunction," the disclosure of which is incorporated by reference. In a further embodiment, sets or "profiles" of pre-selected stimulation parameters can be provided to physicians, which can be selected with the assistance of an external programmer and fine-tuned to a patient's physiological requirements prior to being programmed into the neurostimulator 12 following implantation.

Referring next to FIG. 2B, the therapy lead 13 delivers an electrical signal from the neurostimulator 12 to the vagus nerve 15, 16 via the helical electrodes 14. On a proximal end, the therapy lead 13 has a lead connector 27 that transitions an insulated electrical lead body to a metal connector pin 28. During implantation, the connector pin 28 is guided through the receptacle 25 into the header 24 and securely fastened in place using the set screws 26 to electrically couple the therapy lead 13 to the neurostimulator 12. On a distal end, the therapy lead 13 terminates with the helical electrode 14, which bifurcates into anodic and cathodic electrodes. In one embodiment, the lead connector 27 is manufactured using silicone and the connector pin 28 is made of stainless steel, although other suitable materials could be used, as well. The insulated lead body 13 utilizes a silicone-insulated alloy conductor material.

Preferably, the helical electrodes 14 are placed over the cervical vagus nerve 15, 16 at the location below where the superior and inferior cardiac branches separate from the cervical vagus nerve. In alternative embodiments, the helical electrodes may be placed at a location above where one or both of the superior and inferior cardiac branches separate from the cervical vagus nerve. In one embodiment, the helical electrodes 14 are positioned around the patient's vagus nerve oriented with the end of the helical electrodes 14 facing the patient's head. In an alternate embodiment, the helical electrodes 14 are positioned around the patient's vagus nerve 15, 16 oriented with the end of the helical electrodes 14 facing the patient's heart 17. At the distal end, the insulated electrical lead body 13 is bifurcated into a pair of lead bodies that are connected to a pair of electrodes proper. The polarity of the electrodes could be configured into a monopolar cathode, a proximal anode and a distal cathode, or a proximal cathode and a distal anode.

Figure 5:
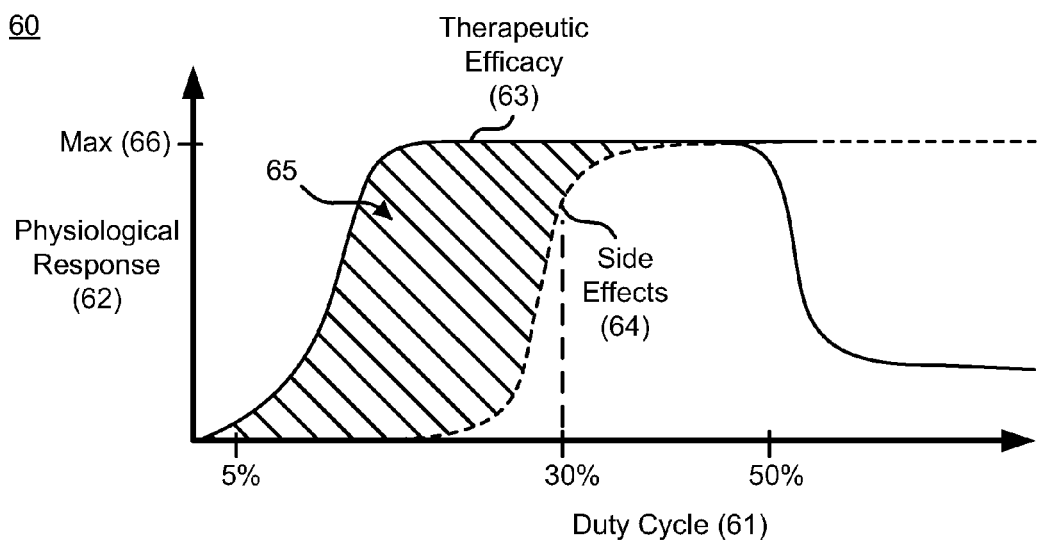
FIG. 5 is a graph showing, by way of example, the relationship between the targeted therapeutic efficacy and the extent of potential side effects resulting from use of the implantable neurostimulator of FIG. 1.

The VNS is delivered as a multimodal set of therapeutic and event-based doses, which are system output behaviors that are pre-specified within the neurostimulator 12 through the stored stimulation parameters and timing cycles implemented in firmware programming and executed by the microprocessor controller. The selections of therapeutic dose and duty cycle are a tradeoff among competing medical considerations. FIG. 5 is a graph 60 showing, by way of example, the relationship between the targeted therapeutic efficacy 63 and the extent of potential side effects 64 resulting from use of the implantable neurostimulator 12 of FIG. 1. The x-axis represents the duty cycle 61. The y-axis represents relative quantified physiological response 62 to VNS therapy. The neurostimulation is delivered bi-directionally and at an intensity that is insufficient to elicit pathological or acute physiological side effects, such as acute cardiac arrhythmias, and without the requirement of an enabling physiological feature or triggering physiological marker, such as heart rate or HRV.

The duty cycle 61 is determined by dividing the stimulation ON time by the sum of the ON and OFF times of the neurostimulator 12 during a single ON-OFF cycle. In a further embodiment, the stimulation time can include ramp-up and ramp-down times respectively preceding and following the ON time during which the neurostimulator 12 delivers the VNS at full output current, such as further described infra with reference to FIG. 6. Ramp-up and ramp-down times may be necessary, for instance, when the stimulation frequency exceeds a minimum threshold. The physiological response 62 can be expressed quantitatively for a given duty cycle 61 as a function of the targeted therapeutic efficacy 63 and the extent of potential side effects 64. The maximum level ("max") 66 of physiological response 62 signifies the highest point of targeted therapeutic efficacy 63 or potential side effects 64.

The therapeutic efficacy 63 represents the intended effectiveness of VNS in provoking a beneficial physiological response, which may be patient- or population-dependent. In contrast to conventional feedback-driven VNS approaches that require an enabling physiological feature to gauge stimuli delivery efficacy, the acute responses and chronic contributing factors need not be (and are likely not) directly observed contemporaneous to VNS delivery. Rather, the contributing factors could be clinically measured over time, such as in-clinic during patient follow up via ECG trace or other metric. As well, in on-going laboratory studies involving canines, increased heart beat regularity during VNS on time, as exhibited through decreased heart rate variability, has been creditably detected through 24-hour Holter monitoring during vagal neural stimulation at a constant continuously-cycling level below a subcardiac threshold, above which there is a slowing of heart rate, conduction velocity or other cardiac artifact.

The therapeutic efficacy 63 can be quantified by assigning values to the realized acute and chronic responses, which together contribute to and synergistically produce the beneficial physiological response. Acute responses include realized changes in HRV, increased coronary flow, reduction in cardiac workload through vasodilation, and improvement in left ventricular relaxation. Chronic factors include improved cardiovascular regulatory function, decreased negative cytokine production, increased baroreflex sensitivity, increased respiratory gas exchange efficiency, favorable gene expression, renin-angiotensin-aldosterone system down-regulation, anti-arrhythmic, anti-apoptotic, and ectopy-reducing anti-inflammatory effects. Still other acute responses and chronic factors are possible.

Beneficial physiological response is generally also considered to be patient dependent, whereby certain of the contributing factors may be more important for one patient as compared to other patients, and no single contributing factor is fully dispositive or conclusive of whether the physiological response is beneficial for any given patient. The contributing factors can be combined in any manner to quantify the relative level of therapeutic efficacy 63, including weighting particular factors more heavily than others, by tailoring the importance of each contributing factor on a patient-specific or population-specific manner, or applying statistical or numeric functions based directly on or derived from realized changes to the patient's physiology. For example, therapeutic goals of achieving an increase of HRV of 10% and decreased negative cytokine production of 3% may be desired for a particular patient with equal weight assigned to each of these goals. Maximum physiological response 66 occurs when these goals are substantially met.

Empirically, therapeutic efficacy 63 steeply increases beginning at around a 5% duty cycle (patient-dependent), as beneficial physiological response 62 is realized, and levels off in a plateau near the maximum level 66 of physiological response 62 at around a 30% duty cycle (patient-dependent), although some patients may require higher (or lower) duty cycles to show similar beneficial physiological response 62. Thereafter, therapeutic efficacy 63 begins decreasing at around a 50% duty cycle (patient-dependent) and continues in a plateau near a 25% physiological response (patient-dependent) through the maximum 100% duty cycle.

The physiological response and occurrence of side effects to different combinations of VNS parameters and timing cycles has been empirically evaluated in pre-clinical work on canines Like the therapeutic efficacy 63, side effects 64 may be patient- or population-dependent and can be quantified by assigning values to the realized acute and chronic side effects. For example, benign acute side effects, such as coughing, could be assigned a low value, while pathological side effects, like bradycardia, could be rated significantly higher to reflect level of severity. In the canine study, the only side effects that were observed were coughing and throat irritation, retching, and bradycardia during 4-6 weeks of gradual titration. Following titration, the only remaining side effect that was observed was bradycardia, which was observed in the following ranges:

Right VNS: In an awake animal, bradycardia was typically observed beginning at approximately 1.25-1.5 mA at a pulse width of 500 μsec and approximately 1.5-1.75 mA at a pulse width 250 μsec, independent of stimulation frequency. However, the magnitude of the current-dependent bradycardia increased with stimulation frequency, with the highest level of bradycardia observed at 20 Hz, the lowest level observed at 10 Hz, and an intermediate level observed at 15 Hz. During sleep, bradycardia was observed at similar parameters as in an awake animal.

Left VNS: In an awake animal, bradycardia was only observed at amplitudes greater than 2.5 mA, and primarily in the 3.0-3.5 mA range. Stimulation frequencies of 15 or 20 Hz were more likely to produce bradycardia at the lower end of that amplitude range, and a stimulation frequency of 10 Hz was more likely to produce bradycardia only at the upper end of the range. In some animals, no bradycardia was observed at any combination of parameters up to the maximum stimulation current of 3.5 mA. During sleep, bradycardia was observed at similar parameters as in an awake animal. Comparable ranges of side effects in humans are expected.

Figure 6:
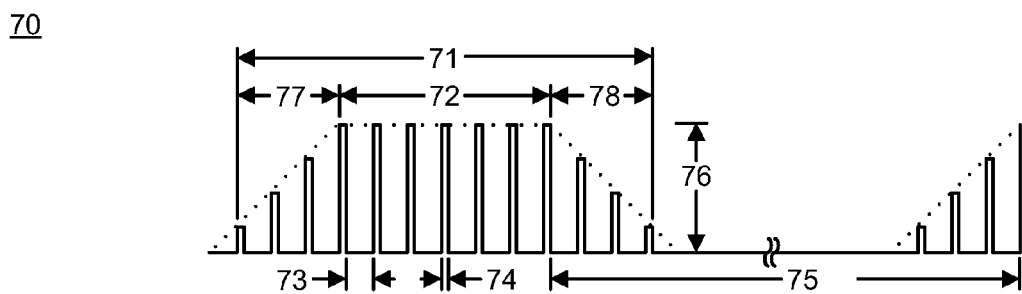
FIG. 6 is a timing diagram showing, by way of example, a stimulation cycle and an inhibition cycle of VNS as provided by implantable neurostimulator of FIG. 1.

In the absence of patient physiology of possible medical concern, such as acute cardiac arrhythmias, VNS is delivered in therapeutic doses that each use alternating cycles of stimuli application (ON) and stimuli inhibition (OFF) that are tuned to activate both afferent and efferent pathways. Stimulation results in parasympathetic activation and sympathetic inhibition, both through centrally-mediated pathways and through efferent activation of preganglionic neurons and local circuit neurons. FIG. 6 is a timing diagram showing, by way of example, a stimulation cycle and an inhibition cycle of VNS 70 as provided by implantable neurostimulator 12 of FIG. 1. The stimulation parameters enable the electrical stimulation pulse output by the neurostimulator 12 to be varied by both amplitude (output current 66) and duration (pulse width 64). The set of stimulation parameters and timing cycle used depends upon the operating mode of therapy desired, which in the described embodiment is the titration mode further described below with reference to FIGS. 7 and 8. Other modes are possible. The number of output pulses delivered per second determines the signal frequency 63. In one embodiment, a pulse width in the range of 100 to 250 μsec is used to deliver between 0.1 and 10 mA of output current at a signal frequency of 5 to 20 Hz, although other therapeutic values could be used as appropriate.

In the simplest case, the stimulation time equals the time period during which the neurostimulator 12 is ON and delivering pulses of stimulation. The OFF time 75 equals the time period occurring in-between stimulation times 71 during which the neurostimulator 12 is OFF and inhibited from delivering stimulation. In one embodiment, the neurostimulator 12 implements either or both of a ramp-up time 77 and a ramp-down time 78 that respectively precede and follow the ON time 72 during which the neurostimulator 12 is ON and delivering pulses of stimulation at the full output current 76. The ramp-up time 77 and ramp-down time 78 are used when the stimulation frequency is at least 10 Hz, although other minimum thresholds could be used, and both ramp-up and ramp-down times 77, 78 last two seconds, although other time periods could also be used. The ramp-up time 77 and ramp-down time 78 allow the strength of the output current 76 of each output pulse to be gradually increased and decreased, thereby avoiding deleterious reflex behavior due to sudden delivery or inhibition of stimulation at a full-strength programmed level of intensity.

As described above, titrating VNS stimulation by having a physician perform each step in the titration creates a medically unnecessary delay in delivering VNS at a full therapeutic intensity to the patient 10. On the other hand, allowing a patient 10 to autotitrate the VNS intensity without physician oversight creates a safety concern. A patient may titrate more aggressively than the physician would like, or may experience painful stimulation if the titration is not performed correctly. Allowing the patient 10 to titrate the VNS stimulation subject to limits set by the patient's physician allows both to avoid the delays associated with visiting the physician's office and to mitigate the safety issues associated with an unsupervised autotitration. FIG. 7 is a flow diagram showing an implantable neurostimulator-implemented method 80 for treatment of chronic cardiac dysfunction with bounded titration in accordance with one embodiment. Initially, after a patient 10 recovers from the implantation of the neurostimulator, a healthcare professional programs the neurostimulator 12 using the external programmer and stores the autotitration operating mode into the recordable memory 29 of the neurostimulator (step 81). As mentioned supra, the operating mode includes one or more parameters defining the highest-intensity dose of VNS stimulation that the patient 10 can command the neurostimulator 12 to deliver during the autotitration process ("maximum stimulation intensity"). This maximum stimulation intensity can be defined either through a single parameter, such as the output current, or through a combination of parameters, with the parameters defining the maximum charge delivered. The autotitration operating mode can include other limitations on the autotiration process, such as a predefined schedule according to which the patient 10 can up-titrate the VNS stimulation. For example, the operating mode can specify that the VNS therapy can be up-titrated once a week for a period of thirty days. The autotitration operating mode can further specify a routine for adjusting the level of VNS stimulation delivered based on the feedback received from the patient 10 regarding whether the up-titrated VNS is tolerable, as further described with reference to FIG. 8. In addition, the operating mode includes the parameters defining an initial dose of VNS stimulation delivered at the start of the autotitration ("titration dose"). In one embodiment, the parameters of the titration dose can be an output current of 0.25 mA, pulse width of 250 μsec, signal frequency of 10 Hz, On time of 14 seconds, and Off time of 1.1 minutes. The intensity of the titration dose is parametrically defined to not exceed the maximum stimulation intensity, which includes the titration dose having one or more of an output current lower or equal to the maximum stimulation intensity output current, a duty cycle lower or equal to the maximum stimulation intensity duty cycle, a frequency lower or equal to the maximum stimulation intensity frequency, and a pulse width shorter or equal to the maximum stimulation intensity pulse width. Finally, the autotitration operating mode is further configured to suspend VNS upon receiving an appropriate signal from the external controller.

Once the autotitration operating mode is received (step 91), the neurostimulator 12 starts therapeutically delivering the titration dose of VNS stimulation (step 82). When the patient 10 uses the external controller to up-titrate the intensity, the neurostimulator 12 receives from the external controller a unique signal, such as a magnetic signal, associated with the command to up-titrate the intensity of the titration dose (step 83). For example, if the patient-operable external controller is an external magnet, the signal can be a unique predefined patter of swipes with the magnet performed by the patient 10 when the patient desires to up-titrate the delivered VNS intensity. Similarly, if the patient-operable external controller is an external electromagnetic controller, such as described in U.S. Pat. No. 8,571,654 cited supra, the patient 10 can press an appropriately-labeled button on the electromagnetic controller when the patient 10 desires to up-titrate the VNS therapy, with the electromagnetic controller sending to the neurostimulator a unique magnetic signal associated with the command to increase the intensity of the titration dose.

Upon receipt of the signal (step 83), the neurostimulator 12 determines whether further increasing the intensity at which the titration dose is delivered would exceed the limits set down by the set down in the autotitration operating mode, and if the limits would be exceeded (step 84), the therapeutic delivery of the titration dose continues at the same intensity as before (step 85), ending the method 80. For example, if increasing the intensity of the titration dose would make the titration dose intensity higher than the maximum intensity dose, the titration dose intensity would not be increased, but would continue at the same level. At that point, the only way for the intensity of the delivered VNS therapy to be increased is for the patient to visit a physician, who will reprogram the neurostimulator 12 with a set of updated limits. For example, if maximum intensity dose is initially defined as having an output current of 1.0 mA, upon autotitrating the intensity once a week for 4 weeks, the output current at which the titration dose is delivered would reach 1.0 mA, requiring the patient to visit the physician's office, where the physician would increase the maximum intensity to, for example, 2.0 mA. After this follow-up visit, the patient could continue autotitrating the VNS therapy until the updated limits are reached.

Similarly, in a further embodiment, if the patient 10 attempts to increase the intensity of the titration dose contrary to other limits, such contrary to the predefined schedule, the neurostimulator 12 will continue delivering the titration dose without increasing the intensity (step 85).

If at step 84 the intensity of the titration dose would not exceed the limits, the intensity of the titration dose delivered to the patient is adjusted as specified in the autotitration operating mode (step 96), such as by increasing one or more parameters defining the titration dose intensity, as further described in detail with reference to FIG. 8. The delivery of the titration dose at the adjusted intensity continues per step 82. While the embodiment described in reference to FIG. 8 describes the autotitration being performed after an implantation (or re-implantation) of the neurostimulator 12, in a further embodiment, the method 80 can be performed under other circumstances.

While physician-imposed limits on autotitration are instrumental in mitigating safety concerns, receiving patient feedback regarding whether an increased intensity of stimulation is tolerable to the patient 10 provides additional safeguards against a patient 10 autotitrating VNS stimulation overly aggressively. Furthermore, adjusting VNS intensity based on the patient feedback presents an alternative to suspending VNS stimulation altogether upon the increased level of stimulation becoming intolerable, thus preserving the continuity of the titration. FIG. 8 is a flow diagram showing a routine 90 for adjusting intensity of VNS therapy during autotitration based on patient feedback for the method 80 of FIG. 7. Continuing with the example of FIG. 8, the initial intensity of the titration dose can be defined using the following parameters: an output current of 0.25 mA, pulse width of 250 μsec, signal frequency of 10 Hz, ON time of 14 seconds, and OFF time of 1.1 minutes. Once the neurostimulator 12 receives the unique signal from the patient-operable external controller associated with a command to up-titrate the titration dose intensity, the neurostimulator 12 increases one of the parameters defining the titration dose intensity, with the titration dose being continuously delivered upon the intensity being adjusted per step 82 (step 91). In the described embodiment, the parameter increased is output current (step 91), with the increase being 0.25 mA. Following the increase of the delivered intensity of the titration dose, the neurostimulator 12 receives feedback from the patient-operable external controller regarding whether the increased intensity titration dose is subjectively tolerable to the patient 10 (step 92). The feedback is received as one or more unique signals from the controller, with differing signals indicating whether the increased intensity of the titration dose is tolerable or not. For example, if the external controller is an external magnet, the patient 10 can indicate whether the increased intensity is tolerable or not by performing different patterns of swipes with the magnet. Similarly, if the patient-operable external controller is an external electromagnetic controller, the controller can transmit unique magnetic signals to the neurostimulator 12 that are associated with the increased intensity being tolerable or intolerable.

If the increased intensity is tolerable to the patient (step 93), the routine 90 returns to step 91, and the output current of the delivered titration dose is further increased (step 91). If the increased intensity is intolerable to the patient (step 103), the output current is reverted to the level that the patient has indicated tolerable, or if the patient has not indicated a tolerable level, to the initial level indicated in the autotitration operating mode (step 94). In the same step, a different parameter of the delivered titration dose, such as pulse width, is increased, with the pulse width increasing to 500 μsec in the described embodiment (step 94). Patient feedback is received regarding whether the titration dose delivered at the increased pulse width is tolerable (step 95), and if the patient 10 indicates that the titration dose at the increased pulse width is tolerable (step 96), another parameter, such as signal frequency, is also increased, with the frequency being increased to 15 Hz in the described embodiment (step 97). If the patient 10 indicates that titration dose delivered at the increased pulse width is intolerable (step 96), the pulse width is reverted to the initial setting and another parameter, such as signal frequency, is increased, with the signal frequency being increased to 15 Hz in the described embodiment (98).

Upon the increase in signal frequency in steps 97 or 98, patient feedback is received regarding whether the increase in frequency is tolerable (step 99). If the delivery of the increase is not tolerable (step 100), the signal frequency is reverted back to the initial level of 10 Hz (step 101), ending the routine 90. Until the next signal associated with a command to up-titrate the VNS therapy is received from the external controller, the titration dose is delivered at the intensity indicated as tolerable by the patient, or if the patient 10 has indicated that the increased intensity is not tolerable, at the initial titration dose intensity. If the delivery of the titration dose at the increased signal frequency is tolerable (step 100), the frequency is further increased to, in the described embodiment, 20 Hz (step 102). Patient feedback is once again received regarding whether the delivery of the titration dose at the further increased signal frequency is tolerable (step 103), and if the titration dose is tolerable (104), the routine 90 terminates, with the neurostimulator 12 continuing to deliver the increased titration dose per step 82 above. If the titration dose delivered at the further increased signal frequency is not tolerable (step 104), the signal frequency is reverted to a level indicated by the patient as tolerable (step 105), ending the routine. Other levels of the parameters can be used in the adjustment of the titration dose intensity. While the described embodiment, multiple parameters are adjusted, in a further embodiment, only a single parameter, such output current, can be adjusted in the routine 90. Furthermore, as described supra, at any moment in the routine 100, the patient 10 can indefinitely suspend VNS therapy using the external controller.

While the invention has been particularly shown and described as referenced to the embodiments thereof, those skilled in the art will understand that the foregoing and other changes in form and detail may be made therein without departing from the spirit and scope.

What is claimed is:

1. A vagus nerve neurostimulator for treatment of chronic cardiac dysfunction, comprising:
   a pulse generator, wherein the pulse generator generates a pulsed electrical signal comprising:
      a signal ON time;
      a signal OFF time;
      an output current;
      a signal frequency;
      a pulse width; and
      a duty cycle defined by dividing the signal ON time by the sum of the signal ON time and signal OFF time;
   a therapy lead;
   an electrode communicatively coupled to the pulse generator via the therapy lead; and
   a recordable memory storing a maximum stimulation intensity and an autotitration operating mode configured to cause the pulse generator to increase an intensity of the pulsed electrical signal up to a level not exceeding the maximum stimulation intensity and to receive, from a patient-operable external controller that allows the patient to provide feedback regarding whether the intensity is intolerable, a first unique signal indicating that the intensity of the delivered pulsed electrical signal is not tolerable to the patient.

2. The vagus nerve neurostimulator according to claim 1, wherein the signal frequency comprises approximately 10 Hz.

3. The vagus nerve neurostimulator according to claim 1, wherein the autotitration mode is configured to cause the pulse generator to apply the pulsed electrical signal to a vagus nerve via the electrode to propagate action potentials in both afferent and efferent directions along the vagus nerve at an intensity that avoids acute physiological side effects.

4. The vagus nerve neurostimulator according to claim 1, wherein the autotitration mode is configured to cause the pulse generator to increase the intensity of the delivered pulsed electrical signal in association with receipt of a second unique signal.

5. The vagus nerve neurostimulator according to claim 1, wherein the autotitration mode is further configured to cause the pulse generator to discontinue the increase in intensity upon receipt of the first unique signal.

6. The vagus nerve neurostimulator according to claim 1, wherein the duty cycle comprises a value in a range of 5% to 20%.

7. The vagus nerve neurostimulator according to claim 1, wherein the pulse generator is configured to deliver the pulsed electrical signal to a vagus nerve via the electrode to induce heart rate variability during the signal ON time.

8. The vagus nerve neurostimulator according to claim 1, further comprising a sensor configured to monitor heart rate.

9. The vagus nerve neurostimulator according to claim 1, wherein:
   the patient-operable external controller is configured to transmit a plurality of signals to the pulse generator including a second unique signal associated with an up-titration command;
   wherein the autotitration operating mode is further configured to cause the pulse generator to continue delivery of the pulsed electrical signal at the intensity up to the level not exceeding the maximum stimulation intensity regardless of receipt of the second unique signal associated with the up-titration command from the patient-operable external controller upon the intensity of the delivered electrical therapeutic stimulation equaling the maximum stimulation intensity.

10. The vagus nerve neurostimulator according to claim 1, wherein the autotitration operating mode is configured to cause the pulse generator to increase the intensity of the pulsed electrical signal upon receipt of a unique tolerance signal indicating that the current intensity of the pulsed electrical signal is tolerable to the patient, and decrease the intensity upon receipt of the first unique signal indicating that the current intensity of the pulsed electrical signal is not tolerable to the patient.

11. A method of operating a vagus nerve neurostimulator to treat chronic cardiac dysfunction, comprising:
   delivering a pulsed electrical signal to a vagus nerve via an electrode coupled to a pulse generator via a therapy lead, the pulsed electrical signal comprising: a signal ON time; a signal OFF time; an output current; a signal frequency; a pulse width; and a duty cycle defined by dividing the signal ON time by the sum of the signal ON time and signal OFF time;
   operating the pulse generator in an autotitration operating mode, the autotitration operating mode comprising increasing an intensity of the pulsed electrical signal up to a level not exceeding a maximum stimulation intensity stored in a recordable memory; and
   receiving, from a patient-operable external controller that allows the patient to provide feedback regarding whether the intensity is intolerable, a first unique signal indicating that the intensity of the delivered pulsed electrical signal is not tolerable to the patient.

12. The method according to claim 11, wherein the signal frequency comprises approximately 10 Hz.

13. The method according to claim 11, wherein the delivering the pulsed electrical signal to the vagus nerve comprises delivering the pulsed electrical signal to the vagus nerve to propagate action potentials in both afferent and efferent directions along the vagus nerve at an intensity that avoids acute physiological side effects.

14. The method according to claim 11, wherein the operating the pulse generator in the autotitration operating mode comprises increasing the intensity of the delivered pulsed electrical signal in association with receipt of a second unique signal.

15. The method according to claim 11, wherein the autotitration mode is configured to discontinue the increase in intensity upon receipt of the first unique signal.

16. The method according to claim 11, wherein the duty cycle comprises a value in a range of 5% to 20%.

17. The method according to claim 11, wherein the delivering the pulsed electrical signal to the vagus nerve induces heart rate variability during the signal ON time.

18. The method according to claim 11, further comprising monitoring a patient heart rate.

19. The method according to claim 11, further comprising:

in response to receiving from the patient-operable external controller a unique tolerance signal indicating that the current intensity of the pulsed electrical signal is tolerable to the patient, increasing the intensity of the pulsed electrical signal; and in response to receiving from the patient-operable external controller the first unique signal indicating that the current intensity of the pulsed electrical signal is not tolerable to the patient, decreasing the intensity of the pulsed electrical signal.

20. The method according to claim 11, further comprising:

continuing delivery of the pulsed electrical signal at the intensity up to the level not exceeding the maximum stimulation intensity regardless of receipt of a second unique signal associated with an up-titration command from a patient-operable external controller upon the intensity of the delivered electrical therapeutic stimulation equaling the maximum stimulation intensity.

* * * * *